(12) United States Patent
Zhang et al.

(10) Patent No.: US 11,981,669 B2
(45) Date of Patent: May 14, 2024

(54) 1,7-NAPHTHYRIDINE DERIVATIVE AND PREPARATION METHOD AND USE THEREFOR

(71) Applicant: CSPC ZHONGQI PHARMACEUTICAL TECHNOLOGY (SHIJIAZHUANG) CO., LTD, Hebei (CN)

(72) Inventors: Yan Zhang, Hebei (CN); Miaomiao Wei, Hebei (CN); Xuejiao Zhang, Hebei (CN); Guorui Mi, Hebei (CN); Hui An, Hebei (CN); Bing Wei, Hebei (CN); Qian Guo, Hebei (CN)

(73) Assignee: CSPC ZHONGQI PHARMACEUTICAL TECHNOLOGY (SHIJIAZHUANG) CO., LTD, Hebei (CN)

( * ) Notice: Subject to any disclaimer, the term of this patent is extended or adjusted under 35 U.S.C. 154(b) by 635 days.

(21) Appl. No.: 17/273,939

(22) PCT Filed: Aug. 29, 2019

(86) PCT No.: PCT/CN2019/103354
§ 371 (c)(1),
(2) Date: Mar. 5, 2021

(87) PCT Pub. No.: WO2020/048380
PCT Pub. Date: Mar. 12, 2020

(65) Prior Publication Data
US 2021/0332043 A1 Oct. 28, 2021

(30) Foreign Application Priority Data
Sep. 5, 2018 (CN) .......................... 201811032376.5

(51) Int. Cl.
*C07D 471/04* (2006.01)
*A61P 7/06* (2006.01)
*A61K 9/00* (2006.01)

(52) U.S. Cl.
CPC .............. *C07D 471/04* (2013.01); *A61P 7/06* (2018.01); *A61K 9/0053* (2013.01)

(58) Field of Classification Search
None
See application file for complete search history.

(56) References Cited

U.S. PATENT DOCUMENTS

2011/0028507 A1* 2/2011 Kim ........................ A61P 31/04
435/375

FOREIGN PATENT DOCUMENTS

| CN | 103608346 A | 2/2014 |
| CN | 108341777 A | 7/2018 |
| WO | 2007090068 A2 | 8/2007 |
| WO | 2007103905 A2 | 9/2007 |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596. (Year: 1996).*

* cited by examiner

*Primary Examiner* — Traviss C McIntosh, III
(74) *Attorney, Agent, or Firm* — NKL Law; Allen Xue

(57) ABSTRACT

A compound represented by formula (I) or a tautomer, an optical isomer, a nitrogen oxide, a solvate, a pharmaceutically acceptable salt or prodrug thereof are useful for treating or relieving an HIF-related and/or EPO-related disease or condition in patient.
The preparation method for the compound, and use of a drug composition containing the compound and the compound or the drug composition in preparation of a drug are also provided.

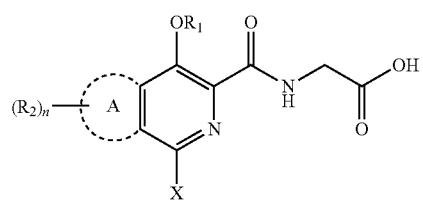

formula (I)

20 Claims, No Drawings

1,7-NAPHTHYRIDINE DERIVATIVE AND PREPARATION METHOD AND USE THEREFOR

TECHNICAL FIELD

The present disclosure relates to the technical field of medical technique, specifically, to a new-type of 1,7-naphthyridine derivative and a preparation method thereof, a pharmaceutical composition comprising the same, and use of the compound or the pharmaceutical composition in the preparation of a medicament.

BACKGROUND ART

Hypoxia inducible factor (HIF) was first discovered by Semenza and Wang in 1992. It is a transcriptional regulator that is universal in human cells and participates in the regulation of various physiological functions of the body. At present, it has been confirmed that more than 100 genes are regulated by HIF, and the encoded products produced by regulation, including erythropoietin (EPO), inducible nitric oxide synthase (iNOS), transferrin, vascular endothelial growth factor (VEGF) and the like, play an important role in erythropoiesis, blood vessel growth, tumor growth, as well as metabolism and cell differentiation.

HIF is a heterodimer composed of a subunit (HIF-α) and β subunit (HIF-β). There are three main subtypes: HIF-1, HIF-2, and HIF-3 Among them, the a subunits are different, which are functional subunits, and determine the biological activity of HIF. The expression of their activity level is affected by oxygen content They cannot exist stably in cells with normal oxygen content, with a half-life of only 5 min. and, only under hypoxic conditions can they stably exist and then play a role. Whereas, the β subunits are the same, which are structural subunits, and their protein expression is not affected by oxygen content.

Prolyl hydroxylase (PHD) belongs to the dioxygenase superfamily and is a $Fe^{2+}$, 2-oxoglutarate-dependent oxygenase. At present, 4 subtypes have been found, namely PHD1, PHD2, PHD3 and PHD4. There are many studies on the first three. PHD1 is expressed in the nucleus, PHD2 is expressed in the cytoplasm, and PHD3 is expressed in both the nucleus and the cytoplasm. Current studies have found that HIF-α is a substrate of PHD. PHD is one of important regulators of HIF pathway, and is a rate-limiting enzyme of HIF degradation Under normal oxygen content, it can recognize proline residues Pro402 and Pro564 on HIF-α, to make them hydroxylated, and then ubiquitinated to degrade HIF-α through the mediation of Hippel Lindau protein. However, under hypoxic conditions, the hydroxylation activity of PHD decreases, which hinders the degradation of HIF-α, and causes accumulation and stable expression of HIF-α, so that it is possible to improve heart failure, ischemia, tissue injury and other diseases in patients with anemia, heart disease and kidney disease.

EPO is synthesized and released by the kidney tissue, which can promote the production of red blood cells in the cells, stimulate the hematopoietic function of bone marrow, and improve the state of hypoxia. At present, EPO and recombinant EPO are mainly used to treat anemia caused by chronic kidney disease, cancer chemotherapy and the like. Increasing the level of EPO in the body is of great significance for the improvement of anemia symptoms. The problems of clinical use of EPO include: 1. it is easy to exceed the physiological range of EPO and cause cardiovascular damage: 2. the convenience of injection is poor; 3 there are immunogenic problems and there are certain risks.

By inhibiting PHD, and reducing the degradation of HIF, it is possible to accumulate the expression of HIF and promote the endogenous secretion of EPO, to maintain its level within the physiological range, thereby improving the hematopoietic function of cells. Therefore, the development of small molecule HIF-PHD inhibitors is of great significance for the treatment of renal anemia caused by insufficient secretion of EPO or even inability to synthesize it in the kidney.

So far, some HIF-PHD inhibitors have been developed Among them. Roxadustat from Fibrogen is in the pre-registration stage. Vadadustat from Akebia Therapeutics, Daprodustat from GlaxoSmithKline and Molidustat from Bayer are in phase III clinical studies.

There is still an urgent need to develop small molecule HIF-PHD inhibitors with novel structures, better efficacy and better safety.

SUMMARY OF THE INVENTION

The present disclosure provides a type of HIF-PHD inhibitor compounds with novel structures, which can be used to the treatment of various HIF-related and/or EPO-related diseases or conditions, such as heart failure, ischemia, tissue injury and the like in patients with anemia, heart disease and kidney disease. Specifically, the present disclosure relates to a compound having the structure of formula (I), a preparation method thereof, a pharmaceutical composition comprising the compound, and use of the compound or the pharmaceutical composition in the preparation of a medicament.

In one aspect, the present disclosure relates to a compound represented by formula (I) or a tautomer, optical isomer, N-oxide, solvate, pharmaceutically acceptable salt or prodrug thereof:

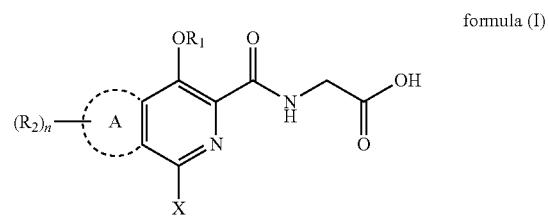

formula (I)

wherein, ring A is a five- to seven-membered nitrogen-containing aromatic heterocycle;

$R_1$ is selected from H or $C_1$-$C_6$ alkyl:

$R_2$ is selected from H, halogen, $C_1$-$C_6$ alkyl or Z—$R_3$; n is selected from 1-3, Z is selected from O or S;

$R_3$ is selected from $C_6$-$C_{14}$ aromatic ring, 5-14 membered aromatic heterocycle, unsubstituted or optionally substituted with one or more substituents. Preferably, the substituents are independently selected from OH, halogen, $C_1$-$C_6$ alkyl, $C_1$-$C_6$ alkoxy, halogen-substituted $C_1$-$C_6$ alkyl, or $R_3$ is selected from H or $C_1$-$C_6$ alkyl;

X is selected from halogen.

In some embodiments, ring A is five- or six-membered nitrogen-containing aromatic heterocycle;

$R_1$ is selected from H or $C_1$-$C_4$ alkyl:

$R_2$ is selected from halogen, $C_1$-$C_4$ alkyl or Z—$R_3$;

$R_3$ is selected from $C_1$-$C_4$ aromatic ring, 5-14 membered aromatic heterocycle, unsubstituted or optionally substituted with one or more substituents, the substituents being independently selected from OH, halogen, $C_1$-$C_4$ alkyl, $C_1$-$C_4$ alkoxy, halogen-substituted $C_1$-$C_4$ alkyl, or $R_3$ is selected from $C_1$-$C_4$ alkyl.

In some embodiments, the A is selected from five- or six-membered aromatic heterocycle only containing one or two nitrogen atoms as heteroatom; the $R_1$ is selected from H; the $R_2$ is selected from halogen or Z—$R_3$; n is selected from 1, 2; Z is selected from O, the $R_3$ is selected from $C_6$-$C_{14}$ aromatic ring, 5-14 membered aromatic heterocycle, unsubstituted or optionally substituted with one or more substituents, the substituents being independently selected from OH, halogen, $C_1$-$C_4$ alkyl, $C_1$-$C_4$ alkoxy, halogen-substituted $C_1$-$C_4$ alkyl.

In some embodiments, the ring A is selected from pyridine, pyrazine, pyridazine, pyrrole, imidazole, the halogen is selected from F, Cl, Br, I.

In some embodiments, $R_2$ is selected from O—$R_3$; $R_1$ is selected from $C_6$-$C_{14}$ aromatic ring or 5-14 membered aromatic heterocycle, optionally substituted with one or more substituents, the substituents being independently selected from OH, halogen, $C_1$-$C_4$ alkyl, $C_1$-$C_4$ alkoxy. More preferably, $R_3$ is selected from phenyl or pyridyl, optionally substituted with one or more substituents, the substituents being independently selected from OH, halogen, $C_1$-$C_4$ alkyl, $C_1$-$C_4$ alkoxy, halogen-substituted $C_1$-$C_4$ alkyl, or $R_3$ is selected from $C_1$-$C_4$ alkyl.

In some embodiments, the compound of the present disclosure is a compound having the structure of formula (II) or a tautomer, optical isomer, N-oxide, solvate, pharmaceutically acceptable salt or prodrug thereof:

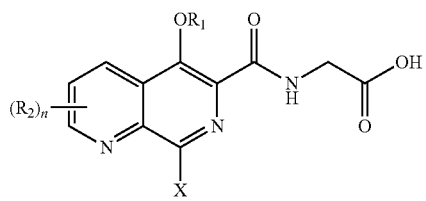

formula (II)

wherein, $R_1$, $R_2$, n, X are as defined above in the formula (I).

In some embodiments, the compound of the present disclosure is a compound having the structure of formula (III) or a tautomer, optical isomer, N-oxide, solvate, pharmaceutically acceptable salt or prodrug thereof:

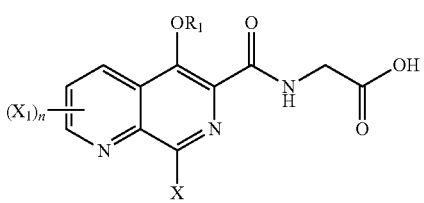

formula (III)

wherein, $R_1$, n, X are as defined above in the formula (I), $X_1$ is independently selected front halogen, the halogen may be selected from F, Cl, Br, I.

In some embodiments, the compound of the present disclosure is a compound having the structure of formula (IIIa) or a tautomer, optical isomer, N-oxide, solvate, pharmaceutically acceptable salt or prodrug thereof:

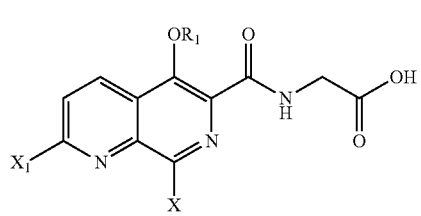

formula (IIIa)

wherein, $R_1$, $X_1$, X are as defined above in the formula (III).

In some embodiments, the compound of the present disclosure is a compound having the structure of formula (IV) or a tautomer, optical isomer, N-oxide, solvate, pharmaceutically acceptable salt or prodrug thereof:

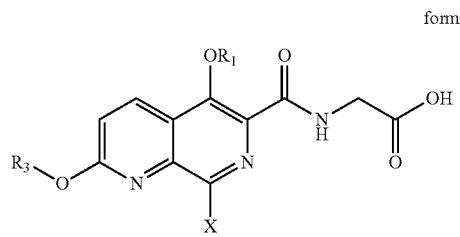

formula (IV)

wherein, $R_1$, $R_3$, X are as defined above in the formula (I).

Preferably, $R_3$ is selected from $C_6$-$C_{14}$ aromatic ring, 5-14 membered aromatic heterocycle, unsubstituted or optionally substituted with one or more substituents, the substituents being independently selected from OH, halogen, $C_1$-$C_6$ alkyl, $C_1$-$C_6$ alkoxy, halogen-substituted $C_1$-$C_6$ alkyl, or $R_3$ is selected from hydrogen or $C_1$-$C_6$ alkyl. More preferably, $R_3$ is selected from phenyl or pyridyl, optionally substituted with one or more substituents, or is selected from $C_1$-$C_6$ alkyl. Still more preferably, $R_3$ is selected from phenyl or pyridyl, optionally substituted with halogen, hydroxy, $C_1$-$C_6$ alkoxy or halogen-substituted $C_1$-$C_4$ alkyl or $R_3$, is selected from $C_1$-$C_4$ alkyl.

In certain embodiments, the compound of the present disclosure is a compound having the structure of formula (V) or a tautomer, optical isomer, N-oxide, solvate, pharmaceutically acceptable salt or prodrug thereof:

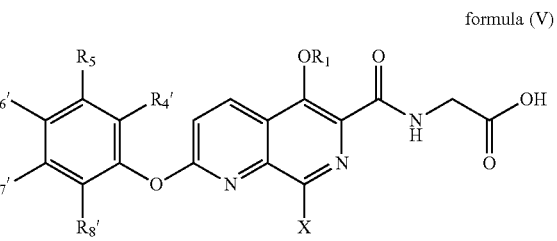

formula (V)

wherein, the $R_1$, X are as defined above in the formula (I); $R_4'$, $R_5'$, $R_6'$, $R_7'$, $R_8'$ are independently selected from H, OH, halogen, $C_1$-$C_6$ alkyl, $C_1$-$C_6$ alkoxy, halogen-substituted $C_1$-$C_6$ alkyl, preferably H, OH, halogen, $C_1$-$C_4$ alkyl, $C_1$-$C_6$ alkoxy, halogen-substituted $C_1$-$C_4$ alkyl.

In some embodiments, the compound of the present disclosure containing OH and COOH moieties may have a prodrug forming moiety linked to it. The prodrug forming moiety is removed by metabolism, and the compound with free hydroxyl or carboxylic acid is released in the body. Prodrug can effectively adjust the pharmacokinetic properties of the compound, such as solubility and lipid-water distribution coefficient, absorption in the gastrointestinal tract, bioavailability, tissue permeability and clearance rate.

Therefore, the present disclosure also provides a compound represented by structural formula (Ib):

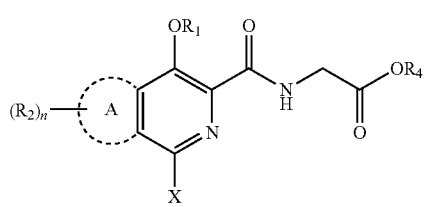

formula (Ib)

wherein, $R_1$, $R_2$, n, X are as defined above in the formula (I);

$R_4$ is selected from $C_1$-$C_6$ alkyl, unsubstituted or substituted with $R_5$, preferably $C_1$-$C_4$ alkyl, unsubstituted or substituted with $R_5$:

$R_5$ is selected from $C_1$-$C_6$ alkoxy-, $C_1$-$C_6$ alkyl (C=O)—, $C_1$-$C_6$ alkyl (C=O)O—, preferably $C_1$-$C_4$ alkoxy-, $C_1$-$C_4$ alkyl (C=O)—, $C_1$-$C_4$ alkyl (C=O)O—.

Preferably, $R_4$ is selected from $C_1$-$C_6$ alkyl (C=O)O—$C_1$-$C_6$ alkyl-, more preferably $C_1$-$C_4$ alkyl (C=O)O—$C_1$-$C_4$ alkyl-, for example, t-butyl-(C=O)O—$CH_2$—.

In some embodiments, the compound of the present disclosure has the structure of formula (IIb):

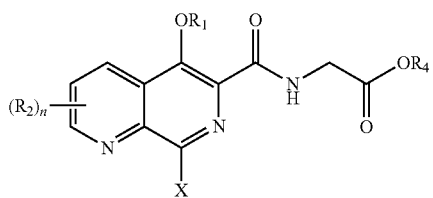

formula (IIb)

wherein, $R_1$, $R_2$, n, X are as defined above in the formula (II);

$R_4$ is as defined above in the formula (Ib).

In some embodiments, the compound of the present disclosure has the structure of formula (IIIb):

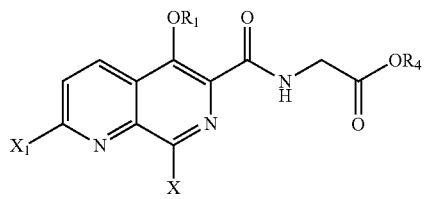

formula (IIIb)

wherein, $R_1$, $X_1$, X are as defined above in the formula (III);

$R_4$ is as defined above in the formula (Ib).

In some embodiments, the compound of the present disclosure has the structure of formula (IVb):

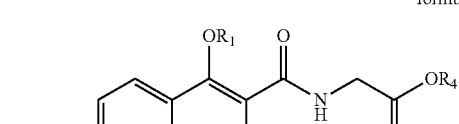

formula (IVb)

wherein, $R_1$, $R_3$, X are as defined above in the formula (IV);

$R_4$ is as defined above in the formula (Ib).

In some embodiments, the compound of the present disclosure has the structure of formula (Vb):

formula (Vb)

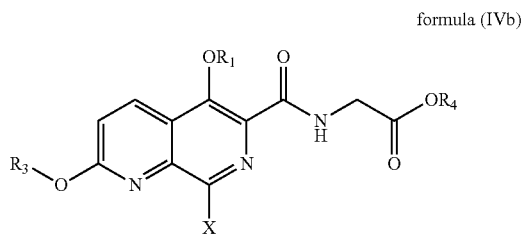

wherein, $R_1$, X, $R_4'$, $R_5'$, $R_6'$, $R_7'$, $R_8'$ are as defined above in the formula (V).

In some embodiments, the compound of the present disclosure has the structure of formula (VIb):

In some embodiments, the compound of the present disclosure further includes tautomers, optical isomers, N-oxides, solvates, pharmaceutically acceptable salts or prodrugs of the compounds having the structures of formula (Ib), formula (IIb), formula (IIIb), formula (IVb), formula (Vb), and formula (VIb).

In some embodiments, the compounds of the present disclosure include the following specific compounds or tautomers, optical isomers, N-oxides, solvates, pharmaceutically acceptable salts or prodrugs thereof:

Link-118

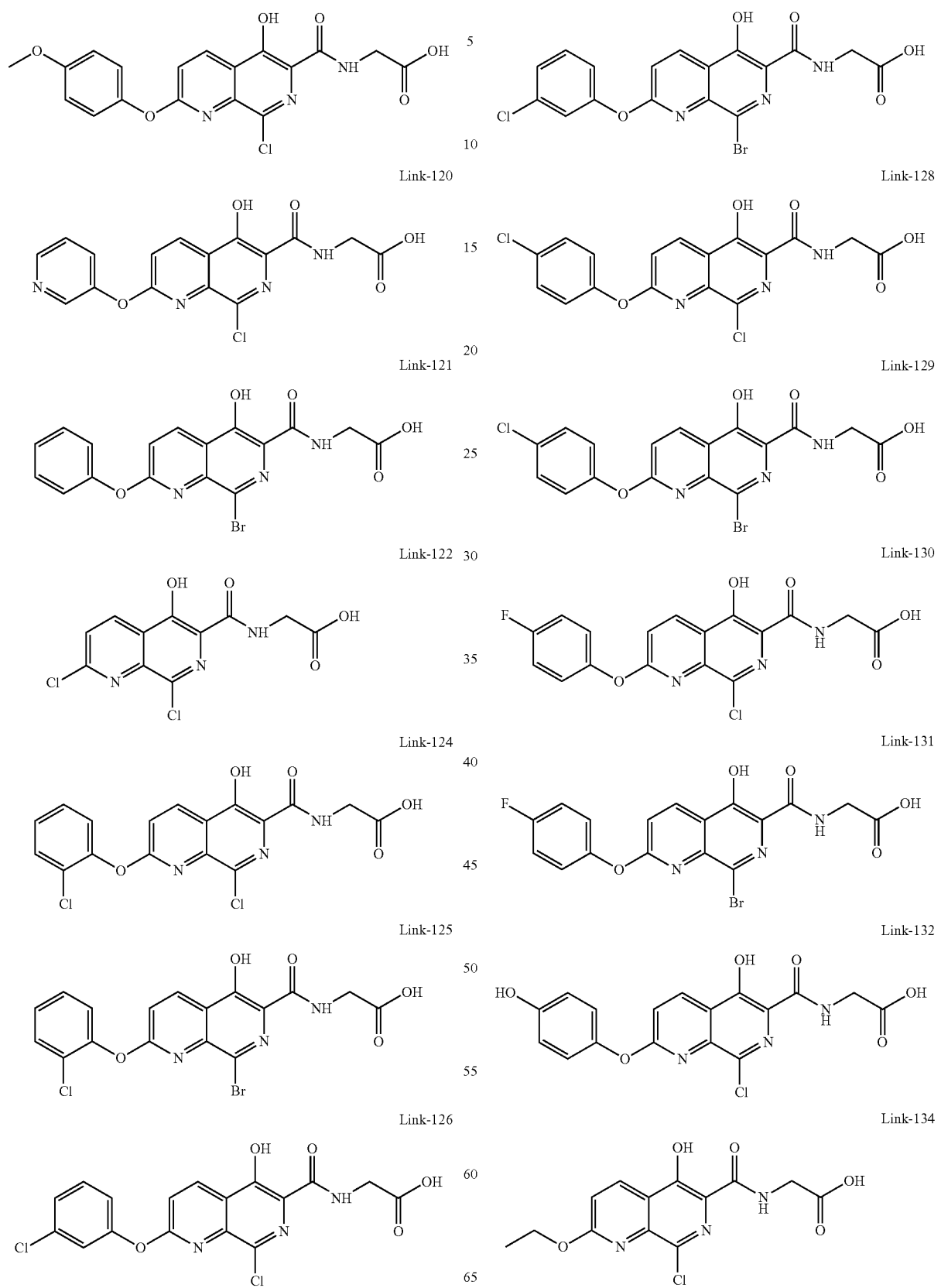

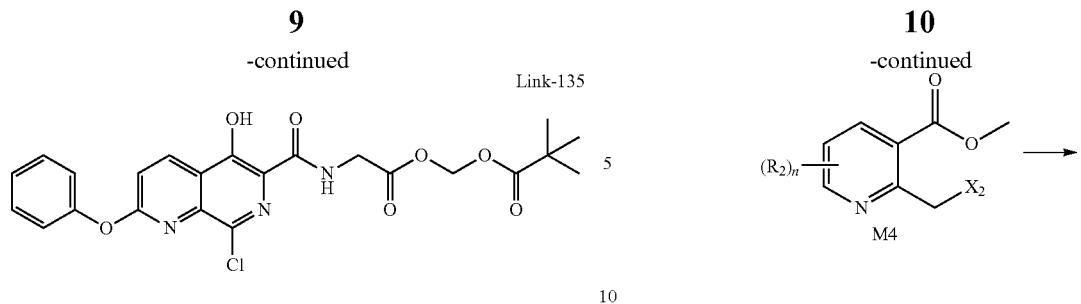

In another aspect, the present disclosure relates to a method for preparing a compound of formula I or a tautomer, optical isomer, N-oxide, solvate, pharmaceutically acceptable salt or prodrug thereof, wherein the method comprises the following steps:

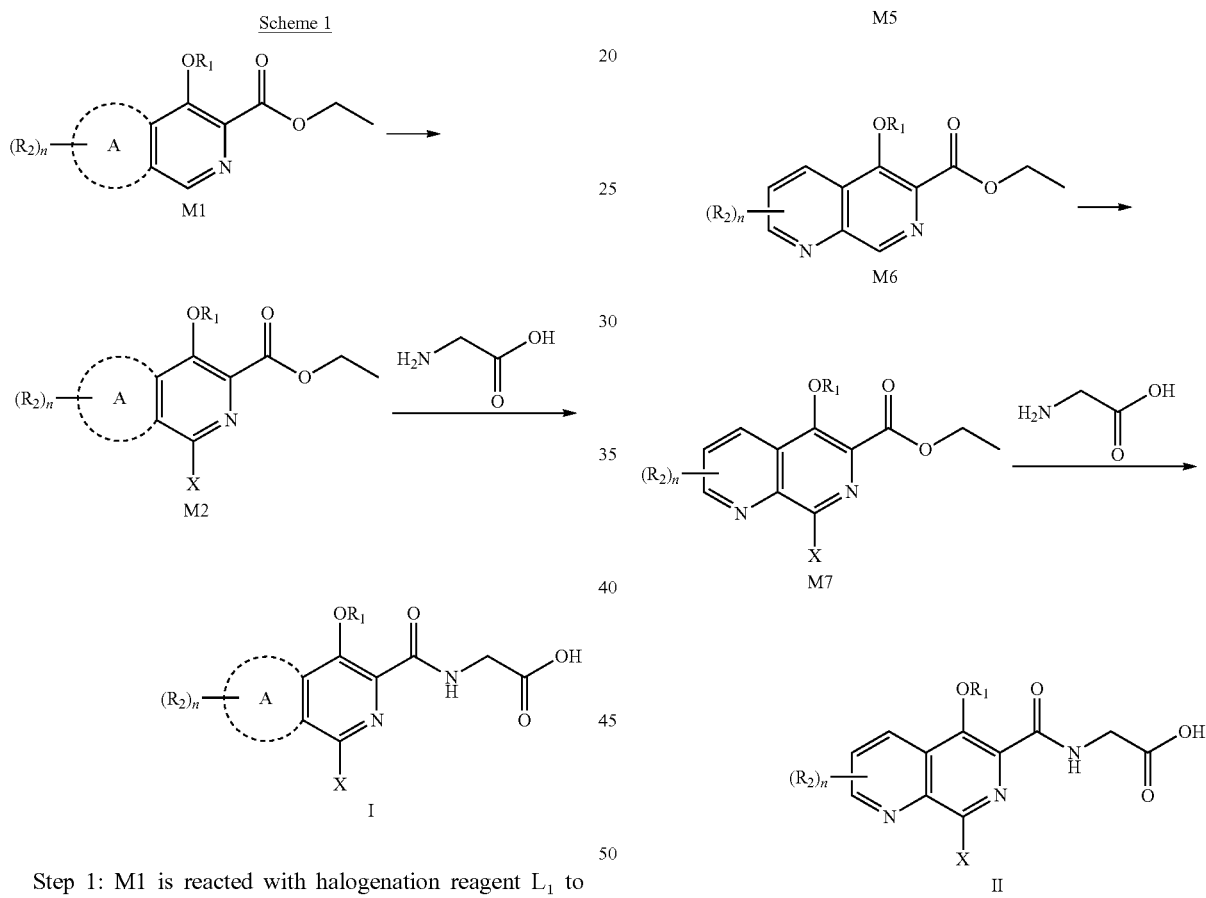

Step 1: M1 is reacted with halogenation reagent $L_1$ to obtain intermediate M2;

Step 2: Intermediate M2 is reacted with glycine under basic conditions to obtain the compound of formula I.

Preferably, for the compound of formula II, the method can also be implemented by the following scheme 2:

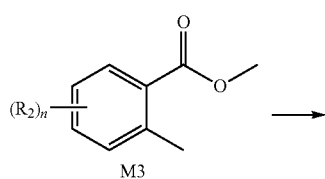

Step 1: M3 is reacted with halogenation reagent $L_1$ to obtain intermediate M4;

Step 2: Intermediate M4 is reacted with ethyl p-toluenesulfonylglycinate to obtain intermediate M5;

Step 3: Intermediate M5 undergoes a ring-closure reaction in the presence of basic reagent A to obtain intermediate M6;

Step 4: Intermediate M6 is reacted with halogenation reagent $L_1$ to obtain intermediate M7;

Step 5: Intermediate M7 is reacted with glycine under basic conditions to obtain a compound of formula II.

Preferably, for the compound of formula IIIa, the method can also be implemented by the following scheme 3:

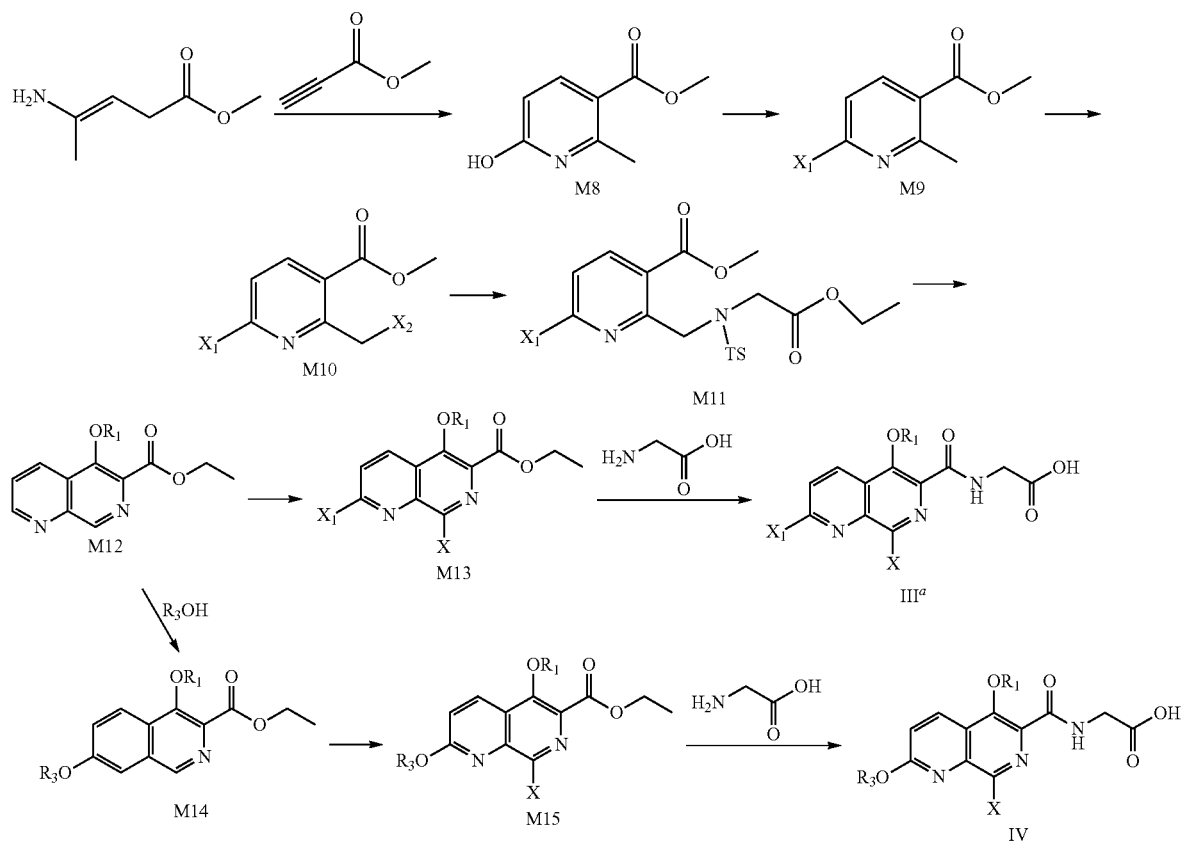

Step 1: Methyl 3-aminocrotonate is reacted with methyl propiolate under basic conditions to produce intermediate M8, and the solvent used may be selected from DMSO, acetonitrile, dimethylformamide and the like, preferably DMSO;
Step 2: Intermediate M8 is reacted with halogenation reagent $L_2$ to obtain intermediate M9;
Step 3: Intermediate M9 is reacted with halogenation reagent $L_1$ to obtain intermediate M10;
Step 4: Intermediate M10 is reacted with ethyl p-toluenesulfonylglycinate to obtain intermediate M11;
Step 5: Intermediate M11 undergoes a ring-closure reaction in the presence of basic reagent A to obtain intermediate M12;
Step 6: Intermediate M12 is reacted with halogenation reagent $L_1$ to obtain intermediate M13;
Step 7: Intermediate M13 is reacted with glycine under basic conditions to obtain compound IIIa.
Preferably, for the compound of formula IV, the method can also be implemented by the following scheme 4:
Step 8: Intermediate M12 is reacted with $R_3OH$ to obtain intermediate M14, further, the reaction conditions can be selected as follows: it is reacted with sodium alkoxide under basic conditions or with substituted or unsubstituted aromatic/aromatic heterocycle-OH compound under the catalysis of Pd to obtain intermediate M14;
Step 9: Intermediate M14 is reacted with halogenation reagent $L_1$ to obtain intermediate M15;
Step 10: Intermediate M15 is reacted with glycine under basic conditions to obtain a compound of formula IV.
Wherein the intermediate M12 can be obtained through the afore-mentioned steps or is commercially available.

For example, intermediate M12 can be obtained through steps 1-5 in the afore-mentioned scheme 3.
In the above schemes, preferably, $X_2$ is selected from halogen, such as F, Cl, Br, I; the halogenation reagent $L_1$ is selected from N-bromosuccinimide, N-chlorosuccinimide, dibromohydantoin, trichloroisocyanuric acid and the like; the halogenation reagent $L_2$ is selected from phosphorus oxychloride, phosphorus oxybromide, thionyl chloride and the like; the basic reagent A is selected from sodium ethoxide, sodium methoxide, sodium hydride, potassium carbonate, cesium carbonate, the basic conditions can be further selected to be the above-defined basic reagent A; the sodium alkoxide is selected from sodium $C_1$-$C_4$ alkoxide, such as sodium methoxide and sodium ethoxide.
In the above schemes, the ethyl p-toluenesulfonylglycinate raw material is prepared by the following method p-toluenesulfonyl halide, ethyl glycinate or a salt thereof are dissolved in a solvent, and stirred while added pyridine dropwise until the reaction is completed. The salt of the ethyl glycinate is preferably ethyl glycinate hydrochloride, and the reaction solvent is preferably dichloromethane.
In the above schemes, in the reaction between methyl 3-aminocrotonate and methyl propiolate, the molar ratio of the methyl 3-aminocrotonate to the methyl propiolate is 1:2 to 2:1, preferably 1:(1-1.2), the reaction process includes (1) methyl 3-aminocrotonate, methyl propiolate, and a solvent are added, and reacted by heating for 6-12 hours, preferably 8 hours, wherein the reaction temperature is 80-120° C.; (2) after the reaction is completed, a basic reagent is added and the reaction is continued for 3-6 hours, preferably 4 hours, wherein the reaction temperature is 80-120° C., the basic reagent is preferably sodium hydroxide, and the molar ratio of the basic reagent to methyl 3-aminocrotonate is 1:2 to 2:1, more preferably 1:(1-1.2).

In the above schemes, in the reaction between the intermediate M8 and the halogenation reagent $L_2$, the molar ratio of the halogenation reagent to the M8 is (2-8):1, preferably 3-5:1, the reaction temperature is 80-120° C., preferably 90-100° C., and the reaction time is 3-8 h, preferably 4-5 h.

In the above schemes, in the reaction between the intermediate M3 or M9 and the halogenation reagent $L_1$, an initiator such as azobisisobutyronitrile or benzoyl peroxide is preferably added, and the reaction solvent may be a halogenated hydrocarbon, preferably dichloromethane, chloroform, carbon tetrachloride, the molar ratio of M3 or M9 $L_1$: initiator is 1:(0.8-1.2):(0.1-0.5); preferably 1:(0.9-1.1):(0.1-0.3); the reaction temperature s 60-100° C., preferably 80-90° C., and the reaction time is 6-10 h, preferably 7-8 h.

In the above schemes, in the reaction between the intermediate M4 or M10 and the ethyl p-toluenesulfonylglycinate, the molar ratio of the M4 or M10 to the ethyl p-toluenesulfonylglycinate is 1:2 to 2:1, preferably 1:1, the reaction solvent is an alcohol reagent, preferably methanol or ethanol; the reaction further includes the subsequent ring-closure reaction, the molar ratio of the basic reagent added in the ring-closure reaction to the M4 or M10 is (1-6):1, preferably (2-5):1, the basic reagent is preferably added in two batches, and the ring-closure reaction is preferably carried out at room temperature, the reaction further includes the following post-treatment: the reaction solution is adjusted to a pH of 6-8, preferably 6-7, and filtered, the filter cake is dissolved with water, and the pH is adjusted to about 6-7, followed by suction filtration to obtain the product.

In the above schemes, in the reaction between the intermediate M12 and $R_3OH$, the Pd catalyst is selected from palladium chloride, palladium acetate, triphenylphosphine palladium and the like, preferably palladium acetate, a basic reagent is further added to the reaction, and the basic reagent can be the basic reagent A defined above, and further preferably cesium carbonate; a phosphine ligand is further added in the reaction, and the phosphine ligand is selected from triphenylphosphine, 1,1'-binaphthyl-2,2'-bisdiphenylphosphine, 2-dicyclohexylphosphino-2,4,6-triisopropylbiphenyl and the like, preferably 1,1'-binaphthyl-2,2'-bisdiphenylphosphine, the solvent for the reaction is preferably DMSO, acetonitrile, dimethylformamide, the reaction temperature is 80-130° C., preferably 90-120° C., more preferably 110° C., and the reaction time is 2-8 hours, preferably 3-6 hours, more preferably 4-5 hours; the reaction further includes the following post-treatment: the reaction solution is poured into a water-organic solvent mixed solution (preferably a water-ethyl acetate mixed solution), stirred, and filtered, the filtrate is subjected to phase separation, the aqueous phase is extracted with an organic solvent, and the organic phases are combined and separated by column chromatography to obtain the product.

In the above schemes, in the reaction between the intermediate M1, M6, M12 or M14 with the halogenation reagent $L_1$ respectively, the reaction solvent is preferably DMSO, acetonitrile, dimethylformamide, more preferably acetonitrile; the reaction temperature is 60-100° C., preferably 70-90° C., more preferably 80° C., and the reaction time is 1-6 hours, preferably 2-5 hours, more preferably 4 hours, the reaction process further includes the following post-treatment: the solvent is evaporated under reduced pressure, and the residue is dissolved with an organic solvent (preferably ethyl acetate), washed with water and separated by column chromatography to obtain the product.

In the above schemes, in the reaction between the intermediate M2, M7, M13 or M15 with glycine respectively, the reaction solvent is preferably DMSO, acetonitrile, dimethylformamide, more preferably DMSO; the reaction temperature is 90-140° C., preferably 100-130° C., more preferably 110-120° C., and the reaction time is 0.5-3 hours, preferably 1-2 hours, more preferably 1.5 hours; the reaction process further includes the following post-treatment: the reaction solution is poured into water, and optionally washed with an organic solvent (preferably ethyl acetate), the pH of the aqueous phase is adjusted to 1-3, preferably 1-2, to precipitate out a solid, which is then dried to obtain the product.

In certain embodiments, the present disclosure also relates to an intermediate compound M15:

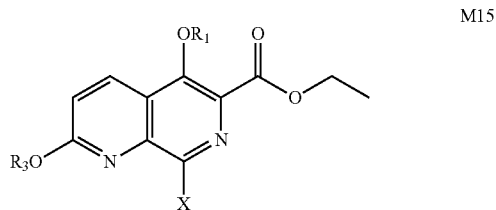

M15 wherein, $R_1$, $R_3$, X are as defined above.

In certain embodiments, the present disclosure also relates to the preparation of a pharmaceutically acceptable salt or solvate of the compound, which is obtained by reacting the compound with a pharmaceutically acceptable salt or solvent according to a conventional method in the art.

In certain embodiments, the present disclosure relates to the preparation of a prodrug of the compound.

The preparation method of the prodrug of the present disclosure includes: reacting a compound of formula I, formula II, formula III/formula IIIa, formula IV or formula V with an esterification reagent under basic conditions to obtain a prodrug compound.

In certain embodiments, the preparation of the prodrug includes reacting a compound of formula I, formula II, formula III/formula IIIa, formula IV or formula V with an esterification reagent under basic conditions to obtain a compound of formula Ib, formula IIb, formula IIIb, Formula IVb, Formula Vb or Formula VIb. The scheme is further illustrated as follows:

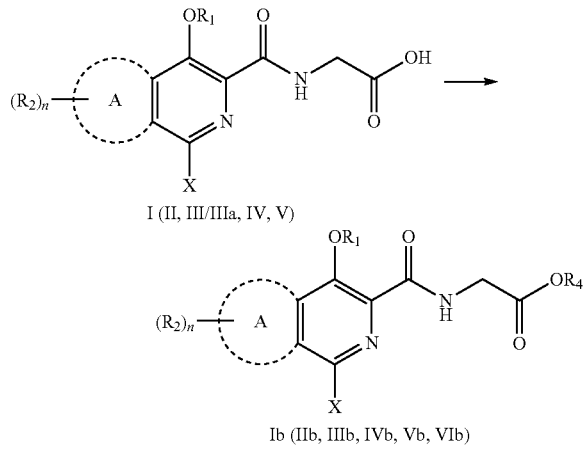

In the above scheme, the basic conditions can be as follows: the basic agent is selected front methylamine, ethylamine, diethylamine, triethylamine, diisopropylethylamine, imidazole, pyridine, 2-methylpyridine, DMAP, DBU and the like, preferably triethylamine and diisopropylethylamine; the solvent in the reaction may include DMF, DMSO, acetonitrile; the molar ratio of the esterification reagent, the compound of formula I (formula II, formula III/formula IIIa, formula IV or formula V) and the basic reagent is 1:(1-2):(1-3), preferably 1:(1-1.5):(1-2.5); the reaction temperature is 30-70° C., preferably 40-60° C., more preferably 50° C., and the reaction time is 3-7 hours, preferably 4-6 hours, more preferably 5 hours.

The reaction process further includes the following post-treatment the reaction solution is poured into a mixture of water and organic solvent (preferably a mixture of water and ethyl acetate), and stirred, the aqueous phase is extracted with an organic solvent, and the organic phases are combined, concentrated under reduced pressure, and separated by column chromatography to obtain the product.

In certain embodiments, the esterification reaction is preferably:

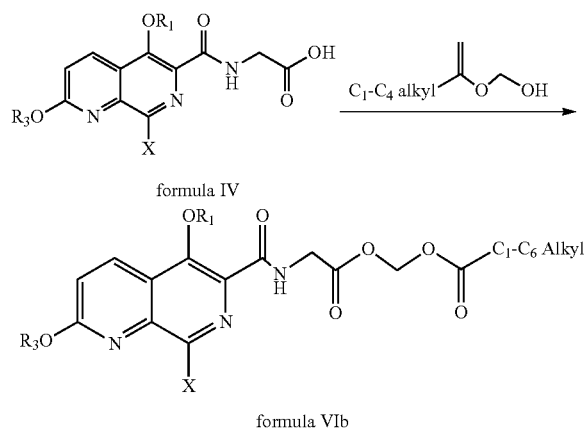

Wherein, Hal is halogen; the halogen can be selected from F, Cl, Br, I; the $C_1$-$C_6$ alkyl (C=O)OCH$_2$-Hal is further preferably $C_1$-$C_4$ alkyl (C=O)OCH$_2$— Hal, more preferably chloromethyl pivalate.

In another aspect, the present disclosure relates to a pharmaceutical composition comprising the compound of the present disclosure or a tautomer, optical isomer, N-oxide, solvate, pharmaceutically acceptable salt or prodrug thereof.

In some embodiments, the pharmaceutical composition of the present disclosure further comprises a therapeutically effective amount of the compound of the present disclosure or a tautomer, optical isomer, N-oxide, solvate, pharmaceutically acceptable salt or prodrug thereof and a pharmaceutically acceptable carrier.

The compound of the present disclosure and the pharmaceutical composition comprising it have HIF-PHD inhibitory activity, and can be used to protect from, treat or alleviate anemia, ischemia, angina, myocardial infarction, metabolic disorders or wound healing diseases in patients. The ischemia includes myocardial ischemia, the anemia includes anemia caused by acute or chronic kidney disease, infection, inflammation, cancer, radiation, toxins, diabetes or surgery. The infection includes AIDS infection.

The compound of the present disclosure and the pharmaceutical composition comprising it can also be used to treat or alleviate HIF-related and/or EPO-related diseases or conditions in patients, for example, to promote endogenous EPO production and to stabilize HIFα.

In another aspect, the present disclosure relates to use of the compound of the present disclosure or a tautomer, optical isomer, N-oxide, solvate, pharmaceutically acceptable salt or prodrug thereof in the preparation of a medicament for treating or alleviating HIF-related and/or EPO-related diseases or conditions in patients.

In another aspect, the present disclosure relates to use of a pharmaceutical composition comprising the compound of the present disclosure or a tautomer, optical isomer, N-oxide, solvate, pharmaceutically acceptable salt or prodrug thereof in the preparation of a medicament for treating or alleviating HIF-related and/or EPO-related diseases or conditions in patients.

In some embodiments, the medicament is used to protect from, treat, or alleviate diseases mediated at least in part by HIF prolyl hydroxylase or the medicament is used to treat diseases that require inhibition of the effect of HIF-PHD.

In some embodiments, the medicament is used to protect from, treat, or alleviate anemia, ischemia, angina, myocardial infarction, metabolic disorders or wound healing diseases in patients. The ischemia includes myocardial ischemia, the anemia includes anemia caused by acute or chronic kidney disease, infection, inflammation, cancer, radiation, toxins, diabetes or surgery. The infection includes AIDS infection. Anemic conditions may further be related to procedures or treatments including, for example, radiation therapy, chemotherapy, dialysis, and surgery. In addition, anemia is related to abnormal hemoglobin and/or red blood cells, such as those found in microcytic anemia, hypochromic anemia, aplastic anemia and other disorders.

In some embodiments, the medicament is preferably used to treat renal anemia diseases or conditions.

In some embodiments, the medicament is used to treat or alleviate HIF-related and/or EPO-related diseases or conditions in patients, for example, to stabilize HIFα; for example, to promote endogenous EPO production. The individual is undergoing preventive or concurrent specific treatment or surgery, for example, an HIV-infected anemia patient being treated with azidothymidine (zidovudine) or other reverse transcription inhibitors, an anemia cancer patient receiving chemotherapy with or without cisplatin or an anemic or non-anemic patient who is planning to undergo surgery. In addition, the compound can be used to increase the endogenous EPO content of an anemic or non-anemic patient who is planning to undergo surgery, thereby reducing the need for allogeneic blood transfusion or promoting blood reserves before surgery.

In some embodiments, the medicament is a medicament that meets the needs to increase iron intake, iron utilization and the like.

EXPLANATION AND DETAILED DESCRIPTION OF TERMS OF THE PRESENT DISCLOSURE

The term "optional" or "optionally" means that the event or situation described later can but does not necessarily occur, and the description includes the situation in which the event or situation occurs and the situation in which it does not occur.

The term "alkyl" includes $C_1$-$C_6$ alkyl, preferably $C_1$-$C_4$ alkyl, which can be straight or branched, and further includes but is not limited to methyl, ethyl, n-propyl, isopropyl, n-butyl, isobutyl, t-butyl. The term also includes the alkyl in all groups that involve alkyl, for example, alkoxy, halogen-substituted alkyl and the like.

The term "aromatic ring" means a monovalent group remained after removing a hydrogen atom from the carbon on the aromatic nucleus of an aromatic hydrocarbon molecule, including $C_6$-$C_{14}$ aromatic ring, and further including but not limited to phenyl and naphthyl.

The term "aromatic heterocycle" or heteroaromatic ring means a monovalent group remained after removing a hydrogen atom from the carbon on the aromatic nucleus of a heteroaromatic compound molecule, wherein the heteroatom is selected from N, O or S, including 5-14 membered aromatic heterocycle. The aromatic heterocycle may be a monocyclic ring or a condensed ring, and may be partially unsaturated. The aromatic heterocycle also includes five- or six-membered nitrogen-containing aromatic heterocycle. The aromatic heterocycle includes but is not limited to pyridine, pyrazine, pyridazine, pyrrole, imidazole, thiophene, furan. The aromatic ring and aromatic heterocycle may be further substituted with a substituent.

The term "halogen" refers to fluorine (F), chlorine (Cl), bromine (Br) or iodine (I).

The term "substituted with one or more substituents" includes, but is not limited to, substitution by one, two, three or four substituents.

The compound of the present disclosure includes the compound or a tautomer, optical isomer, N-oxide, solvate, pharmaceutically acceptable salt or prodrug thereof; the compound further includes compounds represented by formula I, formula II, formula III, formula IIIa, formula IV, formula V, formula Ib, formula IIb, formula IIIb, formula IVb, formula Vb, and formula VIb.

The salt of the compound of the present disclosure preferably includes a pharmaceutically acceptable salt of the compound. The salt can be prepared by any suitable method provided in the literature, for example, with the use of an inorganic acid such as hydrochloric acid, hydrobromic acid, sulfuric acid, nitric acid and phosphoric acid, or with the use of an organic acid such as acetic acid, maleic acid, succinic acid, mandelic acid, fumaric acid, malonic acid, pyruvic acid, oxalic acid, glycolic acid and salicylic acid; pyranonic acids such as glucuronic acid and galacturonic acid; α-hydroxy acids, such as citric acid and tartaric acid; amino acids, such as aspartic acid and glutamic acid; aromatic acids, such as benzoic acid and cinnamic acid; sulfonic acids, such as p-toluenesulfonic acid, ethylsulfonic acid.

In the present disclosure, the solvate is a form of the compound of the present disclosure which, in a solid or liquid state, forms a complex by coordination with a solvent molecule. A hydrate is a specific form of solvate in which the coordination is carried out with water. In the present disclosure, the preferred solvate is a hydrate.

The term "prodrug" or "drug precursor" means a compound that converts into the compound represented by the afore-mentioned formula or the afore-mentioned specific compound in vivo. Such conversion is affected by the hydrolysis of the prodrug in the blood or the enzymatic conversion of the prodrug into the parent structure in the blood or tissue. The prodrug of the present disclosure can be an ester. In the existing invention, the esters that can be used as prodrugs include phenyl esters, aliphatic ($C_{1-24}$) esters, acyloxymethyl esters, carbonates, carbamates, and amino acid esters. For example, a compound in the present disclosure contains hydroxyl/carboxyl, and then it can be acylated to obtain a compound in the form of a prodrug. Other prodrug forms include phosphate esters, for example, phosphate esters obtained by phosphorylation of the parent hydroxyl group.

In the present disclosure, the desired pharmacological effect can be achieved by administering a pharmaceutical composition to a patient in need thereof. For the purpose of the present disclosure, a patient is a mammal, including humans, in need of treatment for a specific condition or disease.

In the present disclosure, the pharmaceutically acceptable carrier may be a carrier that is relatively non-toxic and harmless to the patient at a concentration consistent with the effective activity of the active ingredient, so that any side effect caused by the carrier will not destroy the beneficial effect of the active ingredient. The pharmaceutically effective amount of the compound or a pharmaceutically acceptable salt thereof is preferably an amount that produces a result or effect on the specific condition being treated. Any effective conventional dosage unit form including immediate release, sustained release and timed release preparations can be used. The compound of the present disclosure can be administered together with a pharmaceutically acceptable carrier well known in the art in the following manner, oral, parenteral, local, nasal, eye, sublingual, rectal, vaginal administration, and the like.

For oral administration, the compound of the present disclosure or a pharmaceutically acceptable salt thereof can be formulated into solid or liquid preparations, such as capsules, pills, tablets, troche, lozenge, melt, powder, solution, suspension or emulsion, and can be prepared according to methods known in the art for preparing pharmaceutical compositions. The solid unit dosage form may be a capsule, which may be an ordinary hard capsule or soft capsule, containing, for example, a surfactant, a lubricant, and an inert filler (such as lactose, sucrose, calcium phosphate, and cornstarch).

In the present disclosure, the compound of the present disclosure or a pharmaceutically acceptable salt thereof and a conventional table: excipient(such as lactose, sucrose and corn starch) can also be combined with the following materials and compressed into tablets binders (such as gum arabic, corn starch or gelatin), disintegrants (such as potato starch, alginic acid, corn starch and guar gum, tragacanth gum, gum arabic) used to assist the disintegration and dissolution of tablets after administration, lubricants (such as talc, stearic acid or magnesium stearate, calcium stearate or zinc stearate) used to improve the fluidity of tablet granulation and prevent the tablet material from adhering to the surface of the tablet die and punch, dyes, colorants and flavors (such as peppermint oil, wintergreen oil or cherry flavor) used to improve the organoleptic properties of tablets and make them more acceptable to patients. Suitable excipients for oral liquid dosage forms include dicalcium phosphate and diluents, for example, water and alcohols (such as ethanol, benzyl alcohol and polyvinyl alcohol), with or without the addition of pharmaceutically acceptable surfactants, suspension agents or emulsifiers. Various other substances may be present as coatings or to modify the physical form of the dosage unit. For example, tablets, pills or capsules can be coated with shellac, sugar or both. Dispersible powders and granules are suitable for the preparation of aqueous suspensions. They provide active ingredients mixed with dispersants or wetting agents, suspending agents, and one or more preservatives. Examples of suitable dispersants or wetting agents and suspending agents are those mentioned above. Additional excipients may also be present, such as those flavors and colorants described above.

The pharmaceutical composition of the present disclosure may also be in the form of an oil-in-water emulsion. The oil phase may be a vegetable oil, such as liquid paraffin or a mixture of vegetable oils. Suitable emulsifiers may be (1) natural gums, such as gum arabic and tragacanth gum, (2) natural phospholipids, such as soybean phospholipids and lecithin, and (3) esters or partial esters derived from fatty acids and hexitol anhydrides, such as sorbitan monooleate, (4) condensation products of the partial esters with ethylene oxide, such as polyoxyethylene sorbitan monooleate. The emulsion may also contain sweeteners and flavors. Oily suspensions can be formulated by suspending the active ingredient in vegetable oil (for example, peanut oil, olive oil, sesame oil or coconut oil) or in mineral oil (for example, liquid paraffin). The oily suspension may contain a thickening agent, such as beeswax, hard paraffin or cetyl alcohol. The suspension may also contain one or more preservatives, such as ethyl p-hydoxybenzoate or n-propyl p-hydroxybenzoate; one or more colorants; one or more flavors; and one or more sweeteners, such as sucrose or saccharin. Syrups and elixirs can be formulated with sweeteners (such as glycerol, propylene glycol, sorbitol or sucrose). Such preparations may also contain buffers and preservatives (such as methyl paraben and propyl paraben) as well as flavors and colorants.

The compound of the present disclosure can also be administered parenterally, that is, subcutaneously, intravenously, intraocularly, intrasynovially, intramuscularly or intraperitoneally, at the injection dose of the compound. The injection dose is preferably in a physiologically acceptable diluent containing a pharmaceutical carrier. The pharmaceutical carrier can be a sterile liquid or a mixture of liquids, the liquid is such as water, saline, glucose solution and related sugar solutions, alcohols such as ethanol, isopropanol or cetyl alcohol, glycols such as propylene glycol or polyethylene glycol, glycerol ketals such as 2,2-dimethyl-1,1-dioxolane-4-methanol, ethers such as polyethylene glycol 400 (PEG400), oils, fatty acids, fatty acid esters or fatty acid glycerides or acetylated fatty acid glycerides, the diluent is the added with or without pharmaceutically acceptable surfactants, such as soap or detergent, suspending agents such as pectin, carbomer, methyl cellulose, hypromellose or carboxymethyl cellulose, or emulsifiers and other pharmaceutical adjuvants.

Exemplary oils that can be used in the parenteral preparations of the present disclosure are those derived from petroleum, animal, vegetable or synthetic sources, such as peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal salts, ammonium salts and triethanolamine salts, and suitable detergents include cationic detergents such as dimethyl dialkylammonium halides, alkyl pyridinium halides and alkylamine acetates; anionic detergents such as alkyl sulfonates, aryl sulfonates and olefin sulfonates, alkyl sulfates and alkyl sulfosuccinates, olefin sulfates and olefin sulfosuccinates, ether sulfates and ether sulfosuccinates and monoglyceride sulfates and monoglyceride sulfosuccinates; non-ionic detergents, such as fatty amine oxides, fatty acid alkanolamides and poly(oxyethylene-oxypropylene), ethylene oxide copolymers or propylene oxide copolymers; and amphoteric detergents, such as alkyl-β-aminopropionates and 2-alkylimidazoline quaternary ammonium salts, and mixtures thereof.

The parenteral composition of the present disclosure may generally comprise about 0.5% to about 25% by weight of the active ingredient in solution. Preservatives and buffers can also be used advantageously. In order to minimize or eliminate irritation to the injection site, such compositions may comprise a nonionic surfactant with a hydrophilic-lipophilic balance (HLB) of preferably about 12 to about 17. The amount of surfactant in such preparations is preferably about 5% to about 15% by weight. The surfactant may be a single component having the above-mentioned HLB or a mixture of two or more components having the desired HLB. Exemplary surfactants for parenteral preparations are polyethylene sorbitan fatty acid esters, such as sorbitan monooleate, and a high molecular weight adduct of ethylene oxide and a hydrophobic matrix. The hydrophobic matrix is formed by the condensation of propylene oxide and propylene glycol.

The pharmaceutical composition may be in the form of a sterile aqueous suspension for injection. Such suspensions can be formulated according to known methods using the following materials: suitable dispersants or wetting agents and suspending agents, such as sodium carboxymethyl cellulose, methyl cellulose, hypromellose, sodium alginate, polyvinylpyrrolidone, tragacanth gum and gum arabic; dispersants or wetting agents, which can be natural phospholipids (such as lecithin), condensation products of alkylene oxides and fatty acids (such as polyoxyethylene stearate), condensation products of ethylene oxide and long-chain fatty alcohols (such as PEG-17 cetanol), condensation products of ethylene oxide and partial esters derived from fatty acids and hexitol (such as polyoxyethylene sorbitol monooleate) or condensation products of ethylene oxide and partial esters derived from fatty acids and hexitol anhydride (such as polyoxyethylene sorbitan monooleate).

The sterile injection preparation may also be a sterile solution or suspension for injection in a non-toxic parenterally acceptable diluent or solvent. Usable diluents and solvents are, for example, water. Ringer's solution, isotonic sodium chloride solution, and isotonic glucose solution. In addition, sterile non-volatile oils are routinely used as solvents or suspension media. In this regard, any non-volatile oils with little irritation can be used, including synthetic monoglycerides or diglycerides. In addition, fatty acids (such as oleic acid) can be used in the preparation of injections.

The composition of the present disclosure can also be administered in the form of suppositories for rectal administration of drugs. The composition can be prepared by mixing the drug with a suitable non-irritating excipient that is solid at normal temperature but liquid at rectal temperature and can therefore melt in the rectum to release the drug. Such substance includes, for example, cocoa butter and polyethylene glycol.

Controlled release preparations for parenteral administration include liposomal microspheres, polymer microspheres and polymer gel preparations known in the art.

It may be required or necessary to deliver the pharmaceutical composition to the patient via a mechanical delivery device. The construction and use of the mechanical delivery device for delivering the medicament are well known in the art. For example, a direct technique for administering a drug directly to the brain often involves placing a drug delivery catheter into the patient's ventricular system to bypass the blood-brain barrier.

The compound of the present disclosure can be administered as a single agent or in combination with one or more other agents, wherein the combination does not cause unacceptable adverse reactions. Suitable active agents in the combination include: ACE inhibitors, angiotensin II receptor antagonists, β-receptor blockers, calcium antagonists, PDE inhibitors, mineralocorticoid receptor antagonists, diuretics, aspirin, iron supplements, vitamin B12 and folic acid supplements, statins, digitalis derivatives (digoxin), tumor chemotherapy drugs and antibiotics.

The term "erythropoietin (EPO)-related diseases" refers to any condition associated with lower than normal, abnormal or improper regulation of endogenous erythropoietin. EPO-related diseases include any condition for which an increase in EPO levels will bring beneficial therapeutic effect EPO is a naturally occurring hormone producer, with HIFα, which stimulates the production of red blood cells that carry oxygen throughout the body EPO-related diseases include, but are not limited to, anemia, including anemia related to diabetes, ulcers, renal failure, cancer, infection, dialysis, surgery and chemotherapy; conditions of ischemia and hypoxia, such as arterial occlusive disease, angina, intestinal infarction, pulmonary infarction, cerebral ischemia, and myocardial infarction.

The term "HIF-related diseases" refers to any condition associated with lower than normal, abnormal or improper regulation of HIF. HIF-related diseases include any condition for which an increase in HIF levels will bring beneficial therapeutic effect HIF-related diseases include, but are not limited to, heart disease, stroke, peripheral vascular disease, ulcers, burns, chronic wounds, chronic ischemia, pulmonary embolism, ischemia-reperfusion injury, inflammation, and anemia.

HIF-related and/or EPO-related diseases include, but are not limited to, anemia, ischemia, vascular disease, angina, myocardial ischemia, myocardial infarction, metabolic disorders or wound healing.

The term "diseases mediated at least in pan by HIF prolyl hydroxylase (HIF-PHD)", which can be used interchangeably with the term "HIF prolyl hydroxylase-related diseases", refers to any condition caused by abnormal HIF-PHD, including HIF-related diseases caused by abnormal HIF-PHD. HIF-PHD-related diseases include, but are not limited to, anemia and ischemia.

The term "anemia" refers to any abnormality or deficiency of hemoglobin or red blood cells that results in a decrease in oxygen content in the blood. It can be caused by various conditions, such as acute or chronic kidney disease, infection, inflammation, cancer, radiation, toxins, diabetes and surgery. The infection may be caused by, for example, viruses, bacteria and/or parasites. Inflammation may be caused by infection or autoimmune conditions such as rheumatoid arthritis. Anemia may also be related to blood loss caused by, for example, gastric ulcer, duodenal ulcer, hemorrhoids, gastric cancer or colorectal cancer, trauma, injury, surgical procedures and the like. The formation of anemia may also be related to radiotherapy, chemotherapy and renal dialysis. Anemia is also associated with HIV-infected patients receiving treatment with azidothymidine (zidovudine) or other reverse transcription inhibitors, and can develop in cancer patients receiving chemotherapy (e.g., chemotherapy with or without cisplatin). Aplastic anemia and myelodysplastic syndromes are diseases related to bone marrow failure that leads to reduced red blood cell production. In addition, anemia can be caused by defects or abnormalities in hemoglobin or red blood cells, for example, those found in microcytic anemia, hypochromic anemia and other disorders. Anemia can be caused by obstacles in iron transport, processing and utilization, for example, sideroblastic anemia.

Beneficial Effect of the Present Disclosure (1) The present disclosure provides a type of small molecule HIF-PHD inhibitors with novel structures, which, by inhibiting HIF-PHD, stabilize hypoxia inducible factor HIF-α, and promote the production of EPO. In pharmacological aspects, reticulocyte assay, in vitro and in vivo EPO detection, in vitro HIF protein detection, and PHD1, PHD2, PHD3 enzyme detection and the like are carried out in the present disclosure. From the results, it can be seen that, after administration of the compound, the expression of HIF protein is increased, the production of erythropoietin EPO is increased, the number of reticulocytes in vivo is increased, and the compound has a higher inhibitory activity against PHD1, PHD2, and PHD3. Therefore, the compound of the present disclosure is suitable for a variety of HIF-related and/or EPO-related diseases or conditions, especially for renal anemia diseases or conditions, because renal anemia is mainly caused by reduced red blood cell production, shortened lifespan or missing of red blood cells;

(2) At the same time of having a higher inhibitory activity agsinst HIF-PHD, and significantly increasing the EPO effect, the compounds of the present disclosure are featured with low toxicity, and good drug safety. As shown by the biological activity results, the compounds of the present disclosure all have no obvious inhibitory effect on hERG channels.

(3) As compared with FG-4592, BAY85-3934 comparative drugs and comparative compounds 1-4, the compounds of the present disclosure show improved biological activity as a whole, in particular, the compounds Link-118, Link-121, Link-124, Link-129, Link-130 and the like have significantly higher EPO-increasing effect than those of the comparative drugs.

EMBODIMENTS

The preparation method of the present disclosure will be further described in detail below in conjunction with specific examples. It should be understood that the following examples are only illustrative to illustrate and explain the present disclosure, and should not be construed as limiting the protection scope of the present disclosure. All technologies implemented based on the foregoing contents of the present disclosure are covered by the scope of the present disclosure. In the following examples, unless otherwise specified, all temperatures are in degrees Celsius. Unless otherwise specified, the raw material compounds are synthesized by the methods described herein or are commercially available, and purchased from the following manufacturers: J&K Chemicals. Beijing InnoChem Science & Technology Co., Ltd. Aladdin Bio-Chem, Alfa Aesar, Accela ChemBio Co., Ltd. and the like.

Intermediate: Preparation of ethyl 2-chloro-5-hydroxy-1,7-naphthyridine-6-carboxylate

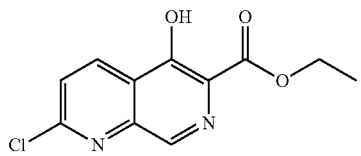 [SMILES: CCOC(=O)c1ncc2nc(Cl)ccc2c1O]

Step 1: Preparation of ethyl 2-(4-methylphenylsulfonylamino) acetate

In 2000 mL of a reaction flask, p-toluenesulfonyl chloride (190.65 g, 1.0 mol), glycine ethyl ester hydrochloride (142.37 g, 1.02 mol), and dichloromethane (1000 mL) were added, stirred at room temperature, then pyridine (174.2, 2.5 mol) was added dropwise, thereafter, the reaction solution was reacted with stirring at room temperature for 45 h. Purified water was added to the reaction flask, and an organic phase was separated. The organic phase was concentrated under reduced pressure to obtain a solid. The solid was dried under vacuum till constant weight, to obtain ethyl 2-(4-methylphenylsulfonylamino) acetate, 200 g, 77.7%.

Step 2: Preparation of methyl 2-methyl-6-hydroxynicotinate

In 1000 mL of a reaction flask, methyl 3-aminocrotonate (127.5 g. 1.11 mol), methyl propiolate (97.8 g, 1.17 mol), and dimethyl sulfoxide (300 mL) were added, heated to 100° C. and reacted for 8 h. To the reaction solution sodium hydroxide (44.3 g, 1.11 mol) was added, and the reaction was continued at 100° C. for 4 h. The reaction solution was cooled, and poured slowly into 1000 mL 1N of hydrochloric acid, to precipitate out a large amount of yellow solid. The reaction solution was adjusted to neutral with sodium carbonate, stirred for 1 h, and subjected to suction filtration. The obtained solid was dried under vacuum till constant weight, to obtain methyl 6-hydroxy-2-methylnicotinate, 140 g, 75.7%.

Step 3: Preparation of methyl 2-methyl-6-chloronicotinate

In 500 mL of a reaction flask, methyl 6-hydroxy-2-methylnicotinate (140 g, 0.84 mol), and phosphorus oxychloride (300 mL) were added in sequence, heated to 100° C. and reacted for 4 h. The reaction solution was concentrated under reduced pressure, and the residue was poured slowly into 1000 mL of ice water, to precipitate out a large amount of gray-black solid. The system was stirred for 1 h, and subjected to suction filtration. The filter cake was dried at room temperature to obtain methyl 2-methyl-6-chloronicotinate, 153 g. 98.7%.

Step 4 Preparation of methyl 2-bromomethyl-6-chloronicotinate

In 1000 mL of a reaction flask, methyl 2-methyl-6-chloronicotinate (153 g, 0.82 mol). N-bromosuccinimide (161 g, 0.90 mol), benzoyl peroxide (40 g, 0.16 mol), and carbon tetrachloride (750 mL) were added, heated to 80° C. and reacted for 8 h. The reaction solution was concentrated under reduced pressure, and 100 mL of petroleum ether was added to the residue, to precipitate out a light yellow solid. The system was stirred for 1 h, and subjected to suction filtration. The filter cake was dried under vacuum till constant weight, to obtain methyl 2-bromomethyl-6-chloronicotinate, 176 g, 80.7%.

Step 5: Preparation of ethyl 2-chloro-5-hydroxy-1,7-naphthyridine-6-carboxylate In 2000 mL of a reaction flask, methyl 2-bromomethyl-6-chloronicotinate (176 g, 0.67 mol), ethyl 2-(4-methylphenylsulfonylamino) acetate (171 g, 0.67 mol), and absolute ethanol (1500 mL) were added, stirred at room temperature, then sodium ethoxide (90 g, 1.34 mol) was added slowly, thereafter, the reaction solution was reacted with stirring at room temperature for 24 h. The reaction solution was adjusted with concentrated hydrochloric acid to a pH of 6~7, filtered, and the filter cake was washed with purified water, and subjected to suction filtration, to obtain a yellow solid ethyl 2-chloro-5-hydroxy-1,7-naphthyridine-6-carboxylate, 40 g, 23.8%.

$^1$H NMR (600 MHz, DMSO-$d_6$) δ; 1.385-1.409(t, 3H), 4.453-4.488(m, 2H), 7.934-7.948(d, J=8.4 Hz, 1H), 8.727-8.741(d, J=8.4 Hz, 1H), 8.902(s. 1H). 11.656(s, 1H).

EXAMPLE 1

(Link-118): Preparation of 2-(2-phenoxy-5-hydroxy-8-chloro-1,7-naphthyridine-6-formamido) Acetic Acid

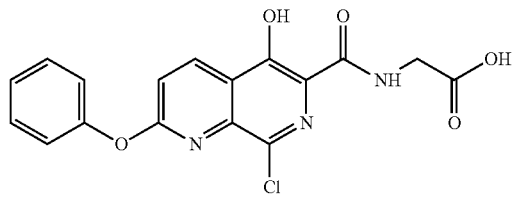 [SMILES: O=C(O)CNC(=O)c1nc(Cl)c2nc(Oc3ccccc3)ccc2c1O]

Step 1: Preparation of ethyl 2-phenoxy-5-hydroxy-1,7-naphthyridine-6-carboxylate In 100 mL of a reaction flask, ethyl 2-chloro-5-hydroxy-1,7-naphthyridine-6-carboxylate (1.5 g, 5.94 mmol), phenol (0.61 g, 6.53 mmol), palladium acetate (0.21 g, 0.95 mmol), 1,1'-binaphthyl-2,2'-bisphenyl phosphine (0.74 g, 1.19 mmol), cesium carbonate (3.87 g, 11.88 mmol), and dimethyl sulfoxide (50 mL) were added, heated to 110° C., and reacted for 4 h. The reaction solution was poured into a mixed solution of 150 mL purified water and 50 mL ethyl acetate, stirred and filtered. The filtrate was subjected to phase separation, and the aqueous phase was further extracted once with 50 mL ethyl acetate. The ethyl acetate layers were combined, separated by column chromatography, eluted with V petroleum ether/V ethyl acetate=5/1, and concentrated to obtain ethyl 2-phenoxy-5-hydroxy-1,7-naphthyridine-6-carboxylate, 0.5 g, 27.2%.

Step 2: Preparation of ethyl 2-phenoxy-5-hydroxy-8-chloro-1,7-naphthyridine-6-carboxylate In 50 mL of a reaction flask, ethyl 2-phenoxy-5-hydroxy-1,7-naphthyridine-6-carboxylate (0.5 g, 1.61 mmol), N-chlorosuccinimide (0.23 g, 1.93 mmol), and acetonitrile (10 mL) were added, heated to 80° C., and reacted for 4 h. The reaction solution was concentrated under reduced pressure, the residue was separated by column chromatography, eluted with V petroleum ether/V ethyl acetate=10/1, and concentrated to obtain an off-white solid ethyl 2-phenoxy-5-hydroxy-8-chloro-1,7-naphthyridine-6-carboxylate, 0.34 g, 60.7%.

Step 3: Preparation of 2-(2-phenoxy-5-hydroxy-8-chloro-1,7-naphthyridine-6-formamido) acetic acid In 50 mL of a reaction flask, ethyl 2-phenoxy-5-hydroxy-8-chloro-1,7-naphthyridine-6-carboxylate (0.34 g, 0.99 mmol), glycine (0.33 g, 2.97 mmol), potassium carbonate (0.4 g, 2.97 mmol), and dimethyl sulfoxide (10 mL) were added, heated to 120° C. and reacted for 1.5 h. The reaction solution was poured into 50 mL purified water, adjusted with concentrated hydrochloric acid to a pH of 1~2, to precipitate out a large amount of solid. The system was stirred for 30 min, and subjected to suction filtration. The filter cake was washed with purified water, and dried under vacuum till constant weight, to obtain an off-white solid 2-(2-phenoxy-5-hydroxy-8-chloro-1,7-naphthyridine-6-formamido) acetic acid, 220 mg, 59.5%.

EXAMPLE 2

(Link-119): Preparation of 2-(2-(4-methoxyphenoxy)-5-hydroxy-8-chloro-1,7-naphthyridine-6-formamido) Acetic Acid

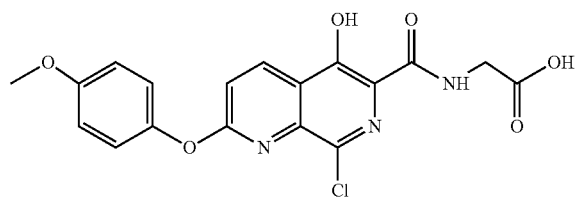 [SMILES: COc1ccc(Oc2ccc3c(O)c(C(=O)NCC(=O)O)nc(Cl)c3n2)cc1]

Step 1: Preparation of ethyl 2-(4-methoxyphenoxy)-5-hydroxy-1,7-naphthyridine-6-carboxylate In 100 mL of a reaction flask, ethyl 2-chloro-5-hydroxy-3,7-naphthyridine-6-carboxylate (1.5 g, 5.94 mmol), p-hydroxyanisole (0.81 g, 6.53 mmol), palladium acetate (0.21 g, 0.95 mmol), 1,1'-binaphthyl-2,2'-bisphenyl phosphine (0.74 g, 1.19 mmol), cesium carbonate (3.87 g, 11.88 mmol), and dimethyl sulfoxide (50 mL) were added, heated to 110° C., and reacted for 4 h. The reaction solution was poured into a mixed solution of 150 mL purified water and 50 mL ethyl acetate, stirred and filtered. The filtrate was subjected to phase separation, and the aqueous phase was further extracted once with 50 mL ethyl acetate. The ethyl acetate layers were combined, separated by column chromatography, eluted with V petroleum ether/V ethyl acetate=5/1, and concentrated to obtain ethyl 2-(4-methoxyphenoxy)-5-hydroxy-1,7-naphthyridine-6-carboxylate, 0.72 g, 35.6%.

Step 2: Preparation of ethyl 2-(4-methoxyphenoxy)-5-hydroxy-8-chloro-1,7-naphthyridine-6-carboxylate In 100 mL of a reaction flask, ethyl 2-(4-methoxyphenoxy)-5-hydroxy-1,7-naphthyridine-6-carboxylate (0.72 g, 2.12 mmol), N-chlorosuccinimide (0.31 g, 2.23 mmol), and acetonitrile (50 mL) were added, heated to 80° C., and reacted for 4 h. The reaction solution was concentrated under reduced pressure, and the residue was separated by column chromatography, eluted with V petroleum ether/V ethyl acetate=10/1, and concentrated to obtain a solid ethyl 2-(4-methoxyphenoxy)-5-hydroxy-8-chloro-1,7-naphthyridine-6-carboxylate, 0.2 g, 25.3%.

Step 3: Preparation of 2-(2-(4-methoxyphenoxy)-5-hydroxy-8-chloro-1,7-napthyridine-6-formamido) Acetic Acid In 50 mL of a reaction flask, ethyl 2-(4-methoxyphenoxy)-5-hydroxy-8-chloro-1,7-naphthyridine-6-carboxylate (020 g, 0.53 mmol), glycine (0.12 g, 1.59 mmol), potassium carbonate (0.22 g, 1.59 mmol), and dimethyl sulfoxide (30 mL) were added, heated to 120° C. and reacted for 1.5 h. The reaction solution was poured into 90 mL purified water, to precipitate out a yellow solid. The system was adjusted with concentrated hydrochloric acid to a pH of 1~2, stirred for 30 min, subjected to suction filtration, and dried under vacuum for 8 h, to obtain an off-white solid2-(2-(4-methoxyphenoxy)-5-hydroxy-8-chloro-1,7-naphthyridine-6-formamido) acetic acid, 170 mg, 77.3%.

EXAMPLE 3

(Link-120): Preparation of 2-(2-(pyrid-3-yloxy)-5-hydroxy-8-chloro-1,7-naphthyridine-6-formamido) Acetic Acid

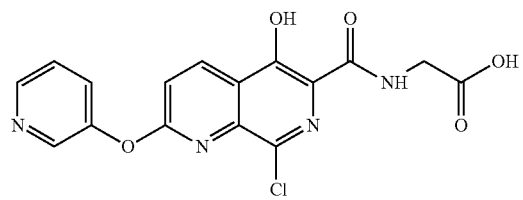 [SMILES: O=C(O)CNC(=O)c1nc(Cl)c2nc(Oc3cccnc3)ccc2c1O]

Step 1: Preparation of ethyl 2-(pyrid-3-yloxy)-5-hydroxy-1,7-naphthyridine-6-carboxylate In 100 mL of a reaction flask, ethyl 2-chloro-5-hydroxy-1,7-naphthyridine-6-carboxylate (1.5 g, 5.94 mmol). 3-hydroxypyridine (0.62 g, 6.53 mmol), palladium acetate (0.21 g, 0.95 mmol), 1,1'-binaphthyl-2,2'-bisphenyl phosphine (0.74 g, 1.19 mmol), cesium carbonate (3.87 g, 11.88 mmol), and dimethyl sulfoxide (50 mL) were added, heated to 110° C., and reacted for 4 h. The reaction solution was poured into a mixed solution of 150 mL purified water and 50 mL ethyl acetate, stirred and filtered. The filter cake was washed with ethyl acetate, the filtrate was subjected to phase separation, and the aqueous phase was further extracted once with 50 mL ethyl acetate. The ethyl acetate layers were combined, separated by column chromatography, eluted with V petroleum ether/V ethyl acetate=5/1, and concentrated to obtain ethyl 2-(pyrid-3-yloxy)-5-hydroxy-1,7-naphthyridine-6-carboxylate, 0.48 g, 25.9%.

Step 2: Preparation of ethyl 2-(pyrid-3-yloxy)-5-hydroxy-8-chloro-1,7-naphthyridine-6-carboxylate In 50 mL of a reaction flask, ethyl 2-(pyrid-3-yloxy)-5-hydroxy-1,7-naphthyridine-6-carboxylate (0.48 g, 1.54 mmol), N-chlorosuccinimide (0.23 g, 1.69 mmol), and acetonitrile (10 mL) were added, heated to 85° C., and reacted for 8 h. The reaction solution was concentrated under reduced pressure, and the residue was separated by column chromatography, eluted with V petroleum ether/V ethyl acetate=10/1, and concentrated to obtain a white solid ethyl 2-(pyrid-3-yloxy)-5-hydroxy-8-chloro-1,7-naphthyridine-6-carboxylate, 0.33 g, 62.3%.

Step 3: Preparation of 2-(2-(pyrid-3-yloxy)-5-hydroxy-8-chloro-1,7-naphthyridine-6-formamido) acetic acid In 50 mL of a reaction flask, ethyl 2-(pyrid-3-yloxy)-5-hydroxy-8-chloro-1,7-naphthyridine-6-carboxylate (0.33 g, 0.95 mmol), glycine (0.22 g, 2.85 mmol), potassium carbonate (0.40 g, 2.85 mmol), and dimethyl sulfoxide (10 mL) were added, heated to 120° C. and reacted for 1.5 h. The reaction solution was poured into 30 mL purified water, adjusted with concentrated hydrochloric acid to a pH of 1~2, to precipitate out a solid. The system was stirred for 30 min, and subjected to suction filtration. The obtained solid was dried under vacuum till constant weight, to obtain a light yellow solid 2-(2-(pyrid-3-yloxy)-5-hydroxy-8-chloro-1,7-naphthyridine-6-formamido) acetic acid, 18 mg, 5.0%.

EXAMPLE 4

(Link-121): Preparation of 2-(2-phenoxy-5-hydroxy-8-bromo-1,7-naphthyridine-6-formamido) Acetic Acid

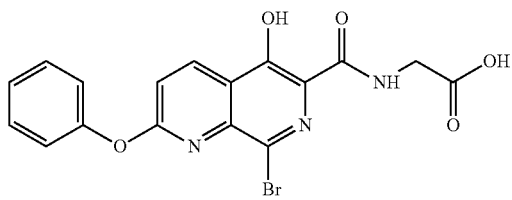 [SMILES: O=C(O)CNC(=O)c1nc(Br)c2nc(Oc3ccccc3)ccc2c1O]

Step 1: Preparation of ethyl 2-phenoxy-5-hydroxy-1,7-naphthyridine-6-carboxylate In 50 mL of a reaction flask, ethyl 2-chloro-5-hydroxy-1,7-naphthyridine-6-carboxylate (1.0 g, 3.96 mmol), phenol (0.39 g, 4.16 mmol), palladium acetate (0.14 g, 0.63 mmol). 1,1'-binaphthyl-2,2'-bisphenyl phosphine (0.5 g, 0.79 mmol), cesium carbonate (2.58 g, 7.92 mmol), and dimethyl sulfoxide (10 mL) were added, heated to 100° C., and reacted for 4 h. The reaction solution was poured into a mixed solution of 30 mL purified water and 20 mL ethyl acetate, stirred and filtered. The filtrate was subjected to phase separation, and the aqueous phase was further extracted once with 20 mL ethyl acetate. The ethyl acetate layers were combined, separated by column chromatography, eluted with V petroleum ether/V ethyl acetate=5/1, and concentrated to obtain ethyl 2-phenoxy-5-hydroxy-1,7-naphthyridine-6-carboxylate, 0.2 g, 16.3%.

Step 2: Preparation of ethyl 2-phenoxy-5-hydroxy-8-bromo-1,7-naphthyridine-6-carboxylate In 10 mL of a reaction flask, ethyl 2-phenoxy-5-hydroxy-1,7-naphthyridine-6-carboxylate (0.2 g, 0.64 mmol), N-bromosuccinimide (0.12 g, 0.67 mmol), and acetonitrile (4 mL) were added, heated to 80° C., and reacted for 4 h. The reaction solution was concentrated under reduced pressure, and the residue was separated by column chromatography, eluted with V petroleum ether/V ethyl acetate=10/1, and concentrated to obtain an off-white solid ethyl 2-phenoxy-5-hydroxy-8-bromo-1,7-naphthyridine-6-carboxylate, 0.13 g, 52.0%.

Step 3: Preparation of 2-(2-phenoxy-5-hydroxy-8-bromo-1,7-naphthyridine-6-formamido) acetic acid In 25 mL of a reaction flask, ethyl 2-phenoxy-5-hydroxy-8-bromo-1,7-naphthyridine-6-carboxylate (0.13 g, 0.33 mmol), glycine (0.10 g, 0.99 mmol), potassium carbonate (0.19 g, 0.99 mmol), and dimethyl sulfoxide (7 mL) were added, heated to 120° C. and reacted for 1.5 h. The reaction solution was poured into 30 mL purified water, adjusted with concentrated hydrochloric acid to a pH of 1~2, to precipitate out a large amount of solid. The system was stirred for 30 min, and subjected to suction filtration. The obtained solid was dried under vacuum till constant weight, to obtain an off-white solid 2-(2-phenoxy-5-hydroxy-8-bromo-1,7-naphthyridine-6-formamido) acetic acid, 110 mg, 78.6%.

EXAMPLE 5

(Link-122): Preparation of 2-(2,8-dichloro-5-hydroxy-1,7-naphthyridine-6-formamido) acetic acid

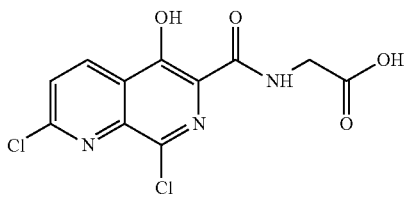 [SMILES: O=C(O)CNC(=O)c1nc(Cl)c2nc(Cl)ccc2c1O]

Step 1: Preparation of ethyl 2,8-dichloro-5-hydroxy-1,7-naphthyridine-6-carboxylate In 50 mL of a reaction flask, ethyl 2-chloro-5-hydroxy-1,7-naphthyridine-6-carboxylate (1.0 g, 3% mmol), N-chlorosuccinimide (0.55 g, 4.16 mmol), and acetonitrile (20 mL) were added, heated to 80° C. and reacted for 2 h. The reaction solution was concentrated under reduced pressure to precipitate out a large amount of solid, followed by filtration to obtain a white solid ethyl 2,8-dichloro-5-hydroxy-1,7-naphthyridine-6-carboxylate, 0.68 g, 59.6%.

Step 2: Preparation of 2-(2,8-dichloro-5-hydroxy-1,7-naphthyridine-6-formamido) acetic acid In 50 mL of a reaction flask, ethyl 2,8-dichloro-5-hydroxy-1,7-naphthyridine-6-carboxylate (0.68 g, 2.40 mmol), glycine (0.53 g, 7.20 mmol), potassium carbonate (0.98 g, 7.20 mmol), and dimethyl sulfoxide (30 mL) were added, heated to 120° C., and reacted for 1.5 h. The reaction solution was poured into 90 mL purified water, and adjusted with concentrated hydrochloric acid to a pH of 1~2, to precipitate out solid. The system was stirred for 30 min, and subjected to suction filtration. The obtained solid was dried under vacuum till constant weight, to obtain 2-(2,8-dichloro-5-hydroxy-1,7-naphthyridine-6-formamido) acetic acid, 0.64 g, 84.2%.

EXAMPLE 6

(Link-124): Preparation of 2-(2-(2-chlorophenoxy)-5-hydroxy-8-chloro-1,7-naphthyridine-6-formamido) Acetic Acid

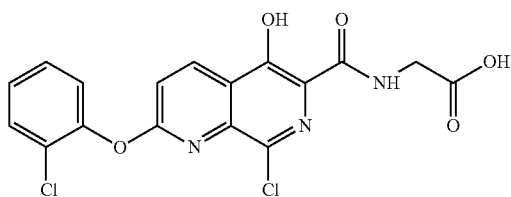 [SMILES: O=C(O)CNC(=O)c1nc(Cl)c2nc(Oc3ccccc3Cl)ccc2c1O]

Step 1: Preparation of ethyl 2-(2-chlorophenoxy)-5-hydroxy-1,7-naphthyridine-6-carboxylate In 100 mL of a reaction flask, ethyl 2-chloro-5-hydroxy-1,7-naphthyridine-6-carboxylate (4.1 g, 16.23 mmol), 2-chlorophenol (2.19 g, 17.04 mmol), palladium acetate (0.29 g, 1.30 mmol), 1,1'-binaphthyl-2,2-bisphenyl phosphine (1.01 g, 1.62 mmol), cesium carbonate (10.57 g, 32.46 mmol), and dimethyl sulfoxide (41 mL) were added, heated to 110° C., and reacted for 12 h. The reaction solution was poured into a mixed solution of 120 mL purified water and 50 mL ethyl acetate, stirred and filtered. The filtrate was subjected to phase separation, and the aqueous phase was further extracted once with 50 mL ethyl acetate. The ethyl acetate layers were combined, separated by column chromatography, eluted with V petroleum ether/V ethyl acetate=7/1, and concentrated to obtain ethyl 2-(2-chlorophenoxy)-5-hydroxy-1,7-naphthyridine-6-carboxylate, 1.4 g, 25.0%.

Step 2: Preparation of ethyl 2-(2-chlorophenoxy)-5-hydroxy-8-chloro-1,7-naphthyridine-6-carboxylate In 50 mL of a reaction flask, ethyl 2-(2-chlorophenoxy)-5-hydroxy-1,7-naphthyridine-6-carboxylate (0.9 g, 2.61 mmol), N-chlorosuccinimide (0.38 g, 2.87 mmol), and acetonitrile (27 mL) were added, heated to 80° C., and reacted for 2 h. The reaction solution was cooled, concentrated under reduced pressure until a large amount of white solid was precipitated out, and the concentration was stopped. The reaction solution was cooled to precipitate for 1 h, and subjected to suction filtration, to obtain a solid ethyl 2-(2-chlorophenoxy)-5-hydroxy-8-chloro-1,7-naphthyridine-6-carboxylate, 0.75 g, 75.8%.

Step 3: Preparation of 2-(2-(2-chlorophenoxy)-5-hydroxy-8-chloro-1,7-naphthyridine-6-formamido) acetic acid In 50 mL of a reaction flask, ethyl 2-(2-chlorophenoxy)-5-hydroxy-8-chloro-1,7-naphthyridine-6-carboxylate (0.75 g, 1.98 mmol), glycine (0.44 g, 5.94 mmol), potassium carbonate (0.81 g, 5.94 mmol), and dimethyl sulfoxide (15 mL) were added, heated to 110° C., and reacted for 2 h. The reaction solution was poured into 150 mL purified water, and adjusted with concentrated hydrochloric acid to a pH of 1~2, to precipitate out a large amount of white solid. The system was stirred for 30 min, and subjected to suction filtration. The obtained solid was dried under vacuum till constant weight, to obtain 2-(2-(2-chlorophenoxy)-5-hydroxy-8-chloro-1,7-naphthyridine-6-formamido) acetic acid, 0.76 g, 93.8%.

EXAMPLE 7

(Link-125): Preparation of 2-(2-(2-chlorophenoxy)-5-hydroxy-8-bromo-1,7-naphthyridine-6-formamido) Acetic Acid

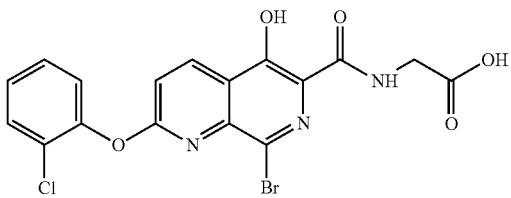 [SMILES: O=C(O)CNC(=O)c1nc(Br)c2nc(Oc3ccccc3Cl)ccc2c1O]

Step 1: Preparation of ethyl 2-(2-chlorophenoxy)-5-hydroxy-1,7-naphthyridine-6-carboxylate In 100 mL of a reaction flask, ethyl 2-chloro-5-hydroxy-1,7-naphthyridine-6-carboxylate (4.1 g, 16.23 mmol), 2-chlorophenol (2.19 g, 17.04 mmol), palladium acetate (0.29 g, 1.30 mmol), 1,1'-binaphthyl-2,2'-bisphenyl phosphine (101 g, 1.62 mmol), cesium carbonate (10.57 g, 32.46 mmol), and dimethyl sulfoxide (41 mL) were added, heated to 110° C., and reacted for 12 h. The reaction solution was poured into a mixed solution of 120 mL purified water and 50 mL ethyl acetate, stirred and filtered. The filtrate was subjected to phase separation, and the aqueous phase was further extracted once with 50 mL ethyl acetate. The ethyl acetate layers were combined, separated by column chromatography, eluted with V petroleum ether/V ethyl acetate=7/1, and concentrated to obtain ethyl 2-(2-chlorophenoxy)-5-hydroxy-1,7-naphthyridine-6-carboxylate, 1.4 g, 25.0%.

Step 2: Preparation of ethyl 2-(2-chlorophenoxy)-5-hydroxy-8-bromo-1,7-naphthyridine-6-carboxylate In 50 mL of a reaction flask, ethyl 2-(2-chlorophenoxy)-5-hydroxy-1,7-naphthyridine-6-carboxylate (0.5 g, 1.45 mmol), N-bromosuccinimide (0.27 g, 1.52 mmol), and acetonitrile (10 mL) were added, heated to 80° C., and reacted for 2 h. The reaction solution was cooled, concentrated under reduced pressure until a large amount of white solid was precipitated out, and the concentration was stopped. The reaction solution was cooled to precipitate for 1 h, and subjected to suction filtration, to obtain a solid ethyl 2-(2-chlorophenoxy)-5-hydroxy-8-bromo-1,7-naphthyridine-6-carboxylate, 0.42 g, 68.9%.

Step 3: Preparation of 2-(2-(2-chlorophenoxy)-5-hydroxy-8-bromo-1,7-naphthyridine-6-formamido) acetic acid In 50 mL of a reaction flask, ethyl 2-(2-chlorophenoxy)-5-hydroxy-8-bromo-1,7-naphthyridine-6-carboxylate (0.42 g, 0.99 mmol), glycine (0.22 g, 2.97 mmol), potassium carbonate (0.41 g, 2.97 mmol), and dimethyl sulfoxide (10 mL) were added, heated to 110° C., and reacted for 2 h. The reaction solution was poured into 100 mL purified water, and adjusted with concentrated hydrochloric acid to a pH of 1~2, to precipitate out a large amount of white solid. The system was stirred for 30 min, and subjected to suction filtration. The obtained solid was dried under vacuum till constant weight, to obtain 2-(2-(2-chlorophenoxy)-5-hydroxy-8-bromo-1,7-naphthyridine-6-formamido), acetic acid 041 g, 91.1%.

EXAMPLE 8

(Link-126): Preparation of 2-(2-(3-chlorophenoxy)-5-hydroxy-8-chloro-1,7-naphthyridine-6-formamido) Acetic Acid

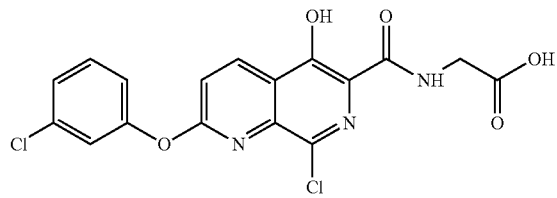 [SMILES: O=C(O)CNC(=O)c1nc(Cl)c2nc(Oc3cccc(Cl)c3)ccc2c1O]

Step 1: Preparation of ethyl 2-(3-chlorophenoxy)-5-hydroxy-1,7-naphthyridine-6-carboxylate In 100 mL of a reaction flask, ethyl 2-chloro-5-hydroxy-1,7-naphthyridine-6-carboxylate (3.0 g, 11.87 mmol), 3-chlorophenol (1.6 g, 12.46 mmol), palladium acetate (0.22 g, 0.95 mmol), 1,1'-binaphthyl-2,2'-bisphenyl phosphine (0.74 g, 1.19 mmol), cesium carbonate (7.74 g, 23.74 mmol), and dimethyl sulfoxide (30 mL) were added, heated to 110° C., and reacted for 12 h. The reaction solution was poured into a mixed solution of 100 mL purified water and 50 mL ethyl acetate, stirred and filtered. The filtrate was subjected to phase separation, and the aqueous phase was further extracted once with 50 mL ethyl acetate. The ethyl acetate layers were combined, separated by column chromatography, eluted with V petroleum ether/V ethyl acetate=5/1, and concentrated to obtain ethyl 2-(3-chlorophenoxy)-5-hydroxy-1,7-naphthyridine-6-carboxylate, 1.9 g, 46.5%.

Step 2; Preparation of ethyl 2-(3-chlorophenoxy)-5-hydroxy-8-chloro-1,7-naphthyridine-6-carboxylate In 50 mL of a reaction flask, ethyl 2-(3-chlorophenoxy)-5-hydroxy-1,7-naphthyridine-6-carboxylate (0.7 g, 2.03 mmol), N-chlorosuccinimide (0.3 g, 2.23 mmol), and acetonitrile (15 mL) were added, heated to 80° C., and reacted for 3 h. The reaction solution was cooled, to precipitate out a large amount of solid. The system was stirred to precipitate for 1 h, and subjected to suction filtration, to obtain a white solid ethyl 2-(3-chlorophenoxy)-5-hydroxy-8-chloro-1,7-naphthyridine-6-carboxylate, 0.58 g, 75.3%.

Step 3: Preparation of 2-(2-(3-chlorophenoxy)-5-hydroxy-8-chloro-1,7-naphthyridine-6-formamido) acetic acid In 50 mL of a reaction flask, ethyl 2-(3-chlorophenoxy)-5-hydroxy-8-chloro-1,7-naphthyridine-6-carboxylate (0.58 g, 1.53 mmol), glycine (0.34 g, 4.59 mmol), potassium carbonate (0.63 g, 4.59 mmol), and dimethyl sulfoxide (10 mL) were added, heated to 110° C., and reacted for 2 h. The reaction solution was poured into 100 mL purified water, and adjusted with concentrated hydrochloric acid to a pH of 1~2, to precipitate out a large amount of white solid. The system was stirred for 30 min, and subjected to suction filtration. The obtained solid was dried under vacuum till constant weight, to obtain 2-(2-(3-chlorophenoxy)-5-hydroxy-8-chloro-1,7-naphthyridine-6-formamido) acetic acid, 0.5 g, 80.6%.

EXAMPLE 9

(Link-127): Preparation of 2-(2-(3-chlorophenoxy)-5-hydroxy-8-bromo-1,7-naphthyridine-6-formamido) Acetic Acid

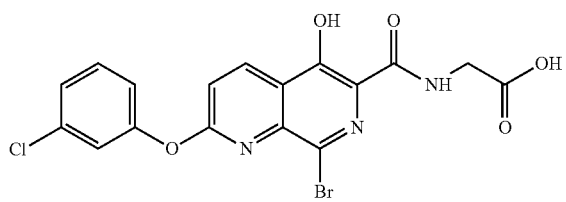 [SMILES: O=C(O)CNC(=O)c1nc(Br)c2nc(Oc3cccc(Cl)c3)ccc2c1O]

Step 1: Preparation of ethyl 2-(3-chlorophenoxy)-5-hydroxy-1,7-naphthyridine-6-carboxylate In 100 mL of a reaction flask, ethyl 2-chloro-5-hydroxy-1,7-naphthyridine-6-carboxylate (3.0 g, 11.87 mmol), 3-chlorophenol (1.6 g, 12.46 mmol), palladium acetate (0.22 g, 0.95 mmol), 1,1'-binaphthyl-2,2'-bisphenyl phosphine (0.74 g, 1.19 mmol), cesium carbonate (7.74 g, 23.74 mmol), and dimethyl sulfoxide (30 mL) were added, heated to 110° C., and reacted for 12 h. The reaction solution was poured into a mixed solution of 100 mL purified water and 50 mL ethyl acetate, stirred and filtered. The filtrate was subjected to phase separation, and the aqueous phase was further extracted once with 50 mL ethyl acetate. The ethyl acetate layers were combined, separated by column chromatography, eluted with V petroleum ether/V ethyl acetate=5/1, and concentrated to obtain ethyl 2-(3-chlorophenoxy)-5-hydroxy-1,7-naphthyridine-6-carboxylate, 1.9 g, 46.5%.

Step 2: Preparation of ethyl 2-(3-chlorophenoxy)-5-hydroxy-8-bromo-1,7-naphthyridine-6-carboxylate In 50 mL of a reaction flask, ethyl 2-(3-chlorophenoxy)-5-hydroxy-1,7-naphthyridine-6-carboxylate (1.17 g, 3.39 mmol), N-bromosuccinimide (0.66 g, 3.73 mmol), and acetonitrile (25 mL) were added, heated to 80° C., and reacted for 2.5 h. The reaction solution was cooled, and concentrated under reduced pressure until a large amount of solid was precipitated out, and the concentration was stopped. The system was stirred to precipitate for 1 h, and subjected to suction filtration, to obtain a yellow solid ethyl 2-(3-chlorophenoxy)-5-hydroxy-8-bromo-1,7-naphthyridine-6-carboxylate, 1.08 g, 75.0%.

Step 3: Preparation of 2-(2-(3-chlorophenoxy)-5-hydroxy-8-bromo-1,7-naphthyridine-6-formamido) acetic acid In 50 mL of a reaction flask, ethyl 2-(3-chlorophenoxy)-5-hydroxy-8-bromo-1,7-naphthyridine-6-carboxylate (1.08 g, 2.55 mmol), glycine (0.58 g, 7.65 mmol), potassium carbonate (1.06 g, 7.65 mmol), and dimethyl sulfoxide (25 mL) were added, heated to 110° C., and reacted for 2 h. The reaction solution was poured into 150 mL purified water, and adjusted with concentrated hydrochloric acid to a pH of 1~2, to precipitate out a large amount of white solid. The system was stirred for 30 min, and subjected to suction filtration. The obtained solid was dried under vacuum till constant weight, to obtain 2-(2-(3-chlorophenoxy)-5-hydroxy-8-bromo-1,7-naphthyridine-6-formamido) acetic acid, 0.69 g, 60.0%.

EXAMPLE 10

(Link-128): Preparation of 2-(2-(4-chlorophenoxy)-5-hydroxy-8-chloro-1,7-naphthyridine-6-formamido) Acetic Acid

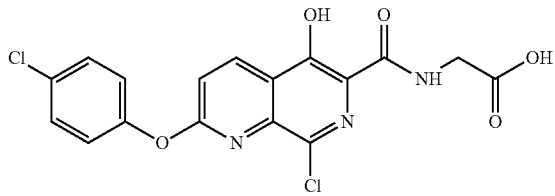 [SMILES: O=C(O)CNC(=O)c1nc(Cl)c2nc(Oc3ccc(Cl)cc3)ccc2c1O]

Step 1: Preparation of ethyl 2-(4-chlorophenoxy)-5-hydroxy-1,7-naphthyridine-6-carboxylate In 100 mL of a reaction flask, ethyl 2-chloro-5-hydroxy-1,7-naphthyridine-6-carboxylate (3.0 g, 11.87 mmol), 4-chlorophenol (1.6 g, 12.46 mmol), palladium acetate (0.22 g, 0.95 mmol), 1,1'-binaphthyl-2,2'-bisphenyl phosphine (0.74 g, 1.19 mmol), cesium carbonate (7.74 g, 23.74 mmol), and dimethyl sulfoxide (30 mL) were added, heated to 110° C., and reacted for 12 h. The reaction solution was poured into a mixed solution of 100 mL purified water and 50 mL ethyl acetate, stirred and filtered. The filtrate was subjected to phase separation, and the aqueous phase was further extracted once with 50 mL ethyl acetate. The ethyl acetate layers were combined, separated by column chromatography, eluted with V petroleum ether/V ethyl acetate=7/1, and concentrated to obtain ethyl 2-(4-chlorophenoxy)-5-hydroxy-1,7-naphthyridine-6-carboxylate, 1.08 g, 26.4%.

Step 2: Preparation of ethyl 2-(4-chlorophenoxy)-5-hydroxy-8-chloro-1,7-naphthyridine-6-carboxylate In 50 mL of a reaction flask, ethyl 2-(4-chlorophenoxy)-5-hydroxy-1,7-naphthyridine-6-carboxylate (0.5 g, 1.45 mmol). N-chlorosuccinimide (0.21 g, 1.60 mmol), and acetonitrile (10 mL) were added, heated to 80° C., and reacted for 3 h. The reaction solution was cooled, to precipitate out a large amount of solid. The system was stirred to precipitate for 1 h, and subjected to suction filtration, to obtain a yellow solid ethyl 2-(4-chlorophenoxy)-5-hydroxy-8-chloro-1,7-naphthyridine-6-carboxylate, 0.25 g, 45.5%.

Step 3: Preparation of 2-(2-(4-chlorophenoxy)-5-hydroxy-8-chloro-1,7-naphthyridine-6-formamido) acetic acid In 25 mL of a reaction flask, ethyl 2-(4-chlorophenoxy)-5-hydroxy-8-chloro-1,7-naphthyridine-6-carboxylate (0.25 g, 0.66 mmol), glycine (0.15 g, 1.98 mmol), potassium carbonate (0.27 g, 1.98 mmol), and dimethyl sulfoxide (5 mL) were added, heated to 110° C., and reacted for 3 h. The reaction solution was poured into 50 mL purified water, and adjusted with concentrated hydrochloric acid to a pH of 1~2, to precipitate out a large amount of white solid. The system was stirred for 30 min. and subjected to suction filtration. The obtained solid was dried under vacuum till constant weight, to obtain 2-(2-(4-chlorophenoxy)-5-hydroxy-8-chloro-1,7-naphthyridine-6-formamido) acetic acid, 0.25 g, 92.6%.

EXAMPLE 11

(Link-129): Preparation of 2-(2-(4-chlorophenoxy)-5-hydroxy-8-bromo-1,7-naphthyridine-6-formamido) Acetic Acid

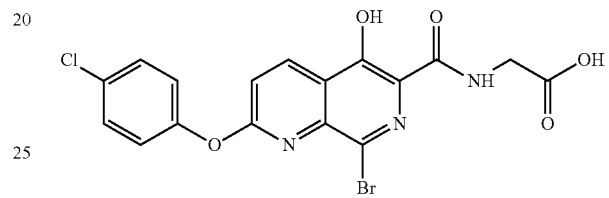

Step 1: Preparation of ethyl 2-(4-chlorophenoxy)-5-hydroxy-1,7-naphthyridine-6-carboxylate In 100 mL of a reaction flask, ethyl 2-chloro-5-hydroxy-1,7-naphthyridine-6-carboxylate (3.0 g, 11.87 mmol), 4-chlorophenol (1.6 g, 12.46 mmol), palladium acetate (0.22 g, 0.95 mmol), 1,1'-binaphthyl-2,2'-bisphenyl phosphine (0.74 g, 1.19 mmol), cesium carbonate (7.74 g, 23.74 mmol), and dimethyl sulfoxide (30 mL) were added, heated to 110° C., and reacted for 12 h. The reaction solution was poured into a mixed solution of 100 mL purified water and 50 mL ethyl acetate, stirred and filtered. The filtrate was subjected to phase separation, and the aqueous phase was further extracted once with 50 mL ethyl acetate. The ethyl acetate layers were combined, separated by column chromatography, eluted with V petroleum ether/V ethyl acetate=7/1, and concentrated to obtain ethyl 2-(4-chlorophenoxy)-5-hydroxy-1,7-naphthyridine-6-carboxylate, 1.08 g, 26.4%.

Step 2: Preparation of ethyl 2-(4-chlorophenoxy)-5-hydroxy-8-bromo-1,7-naphthyridine-6-carboxylate In 25 mL of a reaction flask, ethyl 2-(4-chlorophenoxy)-5-hydroxy-1,7-naphthyridine-6-carboxylate (0.55 g, 1.60 mmol), N-bromosuccinimide (0.31 g, 1.76 mmol), and acetonitrile (5 mL) were added, heated to 80° C., and reacted for 2 h. The reaction solution was cooled, to precipitate out a large amount of solid. The system was stirred to precipitate for 1 h. and subjected to suction filtration, to obtain a white solid ethyl 2-(4-chlorophenoxy)-5-hydroxy-8-bromo-1,7-naphthyridine-6-carboxylate, 0.4 g, 58.8%.

Step 3: Preparation of 2-(2-(4-chlorophenoxy)-5-hydroxy-8-bromo-1,7-naphthyridine-6-formamido) acetic acid In 25 mL of a reaction flask, ethyl 2-(4-chlorophenoxy)-5-hydroxy-8-bromo-1,7-naphthyridine-6-carboxylate (0.4 g, 0.94 mmol), glycine (0.21 g, 2.82 mmol), potassium carbonate (0.39 g, 2.82 mmol), and dimethyl sulfoxide (5 mL) were added, heated to 110° C., and reacted for 3 h. The reaction solution was poured into 50 mL purified water, and adjusted with concentrated hydrochloric acid to a pH of 1~2, to precipitate out a large amount of white solid. The system was stirred for 30 min, and subjected to suction filtration. The obtained solid was dried under vacuum till constant weight, to obtain 2-(2-(4-chlorophenoxy)-5-hydroxy-8-bromo-1,7-naphthyridine-6-formamido) acetic acid (0.4 g, 93.0%).

EXAMPLE 12

(Link-130): Preparation of 2-(2-(4-fluorophenoxy)-5-hydroxy-8-chloro-1,7-naphthyridine-6-formamido) Acetic Acid

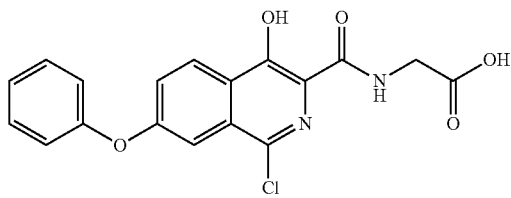 [SMILES: O=C(O)CNC(=O)c1nc(Cl)c2cc(Oc3ccccc3)ccc2c1O]

Step 1: Preparation of ethyl 2-(4-fluorophenoxy)-5-hydroxy-1,7-naphthyridine-6-carboxylate In 100 mL of a reaction flask, ethyl 2-chloro-5-hydroxy-1,7-naphthyridine-6-carboxylate (5.0 g, 19.79 mmol), 4-fluorophenol (2.44 g, 21.77 mmol), palladium acetate (0.71 g, 3.17 mmol), 1,1'-binaphthyl-2,2'-bisphenyl phosphine (2.46 g, 3.96 mmol), cesium carbonate (12.89 g, 39.58 mmol), and dimethyl sulfoxide (25 mL) were added, heated to 110° C., and reacted for 3 h. The reaction solution was poured into a mixed solution of 100 mL purified water and 50 mL ethyl acetate, stirred and filtered. The filtrate was subjected to phase separation, and the aqueous phase was further extracted once with 50 mL ethyl acetate. The ethyl acetate layers were combined, separated by column chromatography, eluted with V petroleum ether/V ethyl acetate=5/1, and concentrated to obtain ethyl 2-(4-chlorophenoxy)-5-hydroxy-1,7-naphthyridine-6-carboxylate 1.2 g, 18.46%.

Step 2: Preparation of ethyl 2-(4-fluorophenoxy)-5-hydroxy-8-chloro-1,7-naphthyridine-6-carboxylate In 25 mL of a reaction flask, ethyl 2-(4-fluorophenoxy)-5-hydroxy-1,7-naphthyridine-6-carboxylate (0.6 g, 1.83 mmol), N-chlorosuccinimide (0.27 g, 2.01 mmol), and acetonitrile (12 mL) were added, heated to 80° C. and reacted for 3 h. The reaction solution was cooled, and concentrated under reduced pressure, until a large amount of solid was precipitated out, and the concentration was stopped. The system was allowed to precipitate under refrigerated conditions overnight, and subjected to suction filtration, to obtain a white solid ethyl 2-(4-fluorophenoxy)-5-hydroxy-8-chloro-1,7-naphthyridine-6-carboxylate, 0.35 g, 53.03%.

Step 3: Preparation of 2-(2-(4-fluorophenoxy)-5-hydroxy-8-chloro-1,7-naphthyridine-6-formamido) acetic acid In 25 mL of a reaction flask, ethyl 2-(4-fluorophenoxy)-5-hydroxy-8-chloro-1,7-naphthyridine-6-carboxylate (0.35 g, 0.96 mmol), glycine (0.22 g, 2.88 mmol), potassium carbonate (0.4 g, 2.88 mmol), and dimethyl sulfoxide (7 mL) were added, heated to 110° C., and reacted for 3 h. The reaction solution was poured into 35 mL purified water, and adjusted with concentrated hydrochloric acid to a pH of 2~3, to precipitate out solid. The system was stirred at room temperature for 1 h, and subjected to suction filtration. The obtained solid was dried under vacuum till constant weight, to obtain 2-(2-(4-fluorophenoxy)-5-hydroxy-8-chloro-1,7-naphthyridine-6-formamido) acetic acid (0.3 g, 78.95%).

EXAMPLE 13

(Link-131): Preparation of 2-(2-(4-fluorophenoxy)-5-hydroxy-8-bromo-1,7-naphthyridine-6-formamido) Acetic Acid

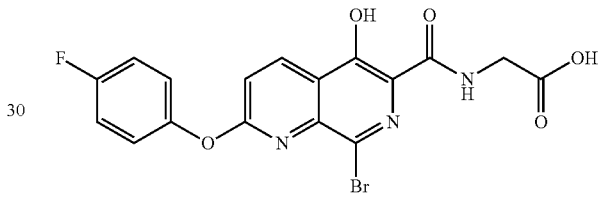

Step 1: Preparation of ethyl 2-(4-fluorophenoxy)-5-hydroxy-1,7-naphthyridine-6-carboxylate In 100 mL of a reaction flask, ethyl 2-chloro-5-hydroxy-1,7-naphthyridine-6-carboxylate (5.0 g, 19.79 mmol), 4-fluorophenol (2.44 g, 21.77 mmol), palladium acetate (0.71 g, 3.17 mmol), 1,1'-binaphthyl-2,2'-bisphenyl phosphine (2.46 g, 3.96 mmol), cesium carbonate (12.89 g, 39.58 mmol), and dimethyl sulfoxide (25 mL) were added, heated to 110° C., and reacted for 3 h. The reaction solution was poured into a mixed solution of 100 mL purified water and 50 mL ethyl acetate, stirred and filtered. The filtrate was subjected to phase separation, and the aqueous phase was further extracted once with 50 mL ethyl acetate. The ethyl acetate layers were combined, separated by column chromatography, eluted with V petroleum ether/V ethyl acetate=5/1, and concentrated to obtain ethyl 2-(4-chlorophenoxy)-5-hydroxy-1,7-naphthyridine-6-carboxylate, 1.2 g, 18.46%.

Step 2: Preparation of ethyl 2-(4-fluorophenoxy)-5-hydroxy-8-bromo-1,7-naphthyridine-6-carboxylate In 25 mL of a reaction flask, ethyl 2-(4-fluorophenoxy)-5-hydroxy-1,7-naphthyridine-6-carboxylate (0.58 g, 1.77 mmol). N-bromosuccinimide (0.35 g, 1.95 mmol), and acetonitrile (12 mL) were added, heated to 80° C., and reacted for 2 h. The reaction solution was cooled, directly separated by column chromatography, eluted with V petroleum ether/V ethyl acetate=6/1, and concentrated to obtain a white solid ethyl 2-(4-fluorophenoxy)-5-hydroxy-8-bromo-1,7-naphthyridine-6-carboxylate, 0.15 g, 20.83%.

Step 3: Preparation of 2-(2-(4-fluorophenoxy)-5-hydroxy-8-bromo-1,7-naphthyridine-6-formamido) acetic acid In 25 mL of a reaction flask, ethyl 2-(4-fluorophenoxy)-5-hydroxy-8-bromo-1,7-naphthyridine-6-carboxylate (0.15 g, 0.37 mmol), glycine (0.083 g, 1.11 mmol), potassium carbonate (0.152 g, 1.11 mmol), and dimethyl sulfoxide (5 mL) were added, heated to 110° C. and reacted for 3 h. The reaction solution was poured into 20 mL purified water, and adjusted with concentrated hydrochloric acid to a pH of 2~3, to precipitate out solid. The system was stirred at room temperature for 1 h. and subjected to suction filtration. The obtained solid was dried under vacuum till constant weight, to obtain 2-(2-(4-fluorophenoxy)-5-hydroxy-8-bromo-1,7-naphthyridine-6-formamido) acetic acid (0.1 g, 62.5%).

EXAMPLE 14

(Link-132): Preparation of 2-(2-(4-hydroxyphenoxy)-5-hydroxy-8-chloro-1,7-naphthyridine-6-formamido) Acetic Acid

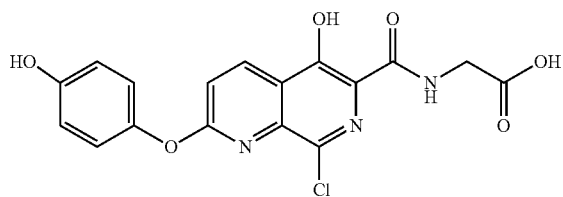 [SMILES: O=C(O)CNC(=O)c1nc(Cl)c2nc(Oc3ccc(O)cc3)ccc2c1O]

Step 1: Preparation of ethyl 2-(4-methoxyphenoxy)-5-hydroxy-1,7-naphthyridine-6-carboxylate In 50 mL of a reaction flask, ethyl 2-chloro-5-hydroxy-1,7-naphthyridine-6-carboxylate (2.0 g, 7.92 mmol), p-hydroxyanisole (0.98 g, 7.92 mmol), palladium acetate 0.28 g, 1.27 mmol), 1,1'-binaphthyl-2,2'-bisphenyl phosphine (0.99 g, 1.58 mmol), cesium carbonate (5.16 g, 15.84 mmol), and dimethyl sulfoxide (15 mL) were added, heated to 110° C., and reacted for 6 h. The reaction solution was poured into a mixed solution of 150 mL purified water and 100 mL ethyl acetate, stirred and filtered. The filtrate was subjected to phase separation, and the aqueous phase was further extracted once with 50 mL ethyl acetate. The ethyl acetate layers were combined, separated by column chromatography, eluted with V petroleum ether/V ethyl acetate/Vdichloromethane=6/1/1-4/1/1, and concentrated to obtain ethyl 2-(4-methoxyphenoxy)-5-hydroxy-1,7-naphthyridine-6-carboxylate, 0.2 g, 7.43%.

Step 2: Preparation of ethyl 2-(4-methoxyphenoxy)-5-hydroxy-8-chloro-1,7-naphthyridine-6-carboxylate In 25 mL of a reaction flask, ethyl 2-(4-methoxyphenoxy)-5-hydroxy-1,7-naphthyridine-6-carboxylate (0.2 g, 0.59 mmol), N-chlorosuccinimide (0.087 g, 0.65 mmol), and acetonitrile (5 mL) were added, heated to 80° C., and reacted for 4 h. The reaction solution was concentrated under reduced pressure, the residue was separated by column chromatography, eluted with V petroleum ether/V ethyl acetate=10/1-5/1, and concentrated to obtain a solid ethyl 2-(4-methoxyphenoxy)-5-hydroxy-8-chloro-1,7-napthyridine-6-carboxylate, 0.2 g, 90.91%.

Step 3: Preparation of ethyl 2-(4-hydroxyphenoxy)-5-hydroxy-8-chloro-1,7-naphthyridine-6-carboxylate In 50 mL of a reaction flask, ethyl 2-(4-methoxyphenoxy)-5-hydroxy-8-chloro-1,7-naphthyridine-6-carboxylate (0.2 g, 1.53 mmol) and dichloromethane (5 mL) were added, and, under the protection of nitrogen, cooled to −5° C. Boron tribromide (1.5 g, 6.13 mmol) was added, and further stirred for 20 min. The reaction solution was heated to room temperature, and the reaction was continued for 2 h. Ice was added to the reaction solution slowly for quenching. The system was stirred for 10 min, adjusted with sodium hydroxide to neutral pH, and extracted twice with 20 mL ethyl acetate. The organic phases were combined, separated by column chromatography, eluted with V petroleum ether/V ethyl acetate=5/1, and concentrated to obtain a solid ethyl 2-(4-hydroxyphenoxy)-5-hydroxy-8-chloro-1,7-naphthyridine-6-carboxylate, 0.13 g, 68.42%.

Step 4: Preparation of 2-(2-(4-hydroxyphenoxy)-5-hydroxy-8-chloro-1,7-naphthyridine-6-formamido) Acetic Acid In 25 mL of a reaction flask, ethyl 2-(4-hydroxyphenoxy)-5-hydroxy-8-chloro-1,7-naphthyridine-6-carboxylate (0.13 g, 0.36 mmol), glycine (0.081 g, 1.08 mmol), potassium carbonate (0.15 g, 1.08 mmol), and dimethyl sulfoxide (5 mL) were added, heated to 110° C. and reacted for 4 h. The reaction solution was poured into 50 mL purified water, and adjusted with concentrated hydrochloric acid to a pH of 2~3, to precipitate out solid. The system was stirred at room temperature for 1 h, and subjected to suction filtration. The obtained solid was dried under vacuum till constant weight, to obtain 2-(2-(4-hydroxyphenoxy)-5-hydroxy-8-chloro-1,7-naphthyridine-6-formamido) acetic acid (0.06 g, 42.86%).

EXAMPLE 15

(Link-134): Preparation of 2-(2-ethoxy-5-hydroxy-8-chloro-1,7-naphthyridine-6-formamido) Acetic Acid

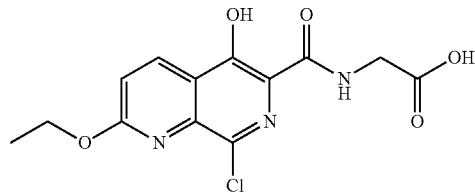 [SMILES: CCOc1ccc2c(O)c(C(=O)NCC(=O)O)nc(Cl)c2n1]

Step 1: Preparation of ethyl 2-ethoxy-5-hydroxy-1,7-naphthyridine-6-carboxylate In 25 mL of a reaction flask, ethyl 2-chloro-5-hydroxy-1,7-naphthyridine-6-carboxylate (0.5 g, 1.98 mmol), sodium ethoxide ethanol solution (2.75 g, 7.99 mmol), and absolute ethanol (5 mL) were added, heated to 90° C., and reacted for 6 h. The reaction solution was concentrated under reduced pressure, and then 100 mL of purified water was added to the residue, followed by adjusting with concentrated hydrochloric acid to a pH of 4. The system was stirred for 1 h, and filtered to obtain a solid ethyl 2-ethoxy-5-hydroxy-1,7-naphthyridine-6-carboxylate (0.36 g, 69.23%).

Step 2: Preparation of ethyl 2-ethoxy-5-hydroxy-8-chloro-1,7-naphthyridine-6-carboxylate In 25 mL of a reaction flask, ethyl 2-ethoxy-5-hydroxy-1,7-naphthyridine-6-carboxylate (0.36 g, 1.37 mmol), N-chlorosuccinimide (0.2 g, 1.51 mmol), and acetonitrile (5 mL) were added, heated to 80° C., and reacted for 4 h. The reaction solution was concentrated under reduced pressure, and the residue was separated by column chromatography, eluted with V petroleum ether/V ethyl acetate=25/1-10/1, and concentrated to obtain a solid ethyl 2-ethoxy-5-hydroxy-8-chloro-1,7-naphthyridine-6-carboxylate, 0.37 g, 90.24%.

Step 3: Preparation of 2-(2-ethoxy-5-hydroxy-8-chloro-1,7-naphthyridine-6-formamido) acetic acid In 25 mL of a reaction flask, ethyl 2-ethoxy-5-hydroxy-8-chloro-1,7-naphthyridine-6-carboxylate (0.37 g, 1.25 mmol), glycine (0.28 g, 3.75 mmol), potassium carbonate (0.52 g, 3.75 mmol), and dimethyl sulfoxide (5 mL) were added, heated to 110° C., and reacted for 3 h. The reaction solution was cooled, poured into 35 mL purified water, adjusted with concentrated hydrochloric acid to a pH of 2~3, to precipitate out solid, and then filtered. The obtained solid was dried under vacuum till constant weight, to obtain a pink solid 2-(2-ethoxy-5-hydroxy-8-chloro-1,7-naphthyridine-6-formamido) acetic acid (0.23 g, 56.10%).

EXAMPLE 16

(Link-135): Preparation of methyl (2-(2-phenoxy-5-hydroxy-8-chloro-1,7-naphthyridine-6-formamido) acetoxy) pivalate

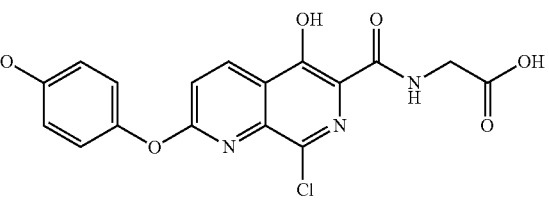

Step 1: Preparation of methyl (2-(2-phenoxy-5-hydroxy-8-chloro-1,7-naphthyridine-6-formamido) acetoxy) pivalate In 25 mL of a reaction flask, 2-(2-phenoxy-5-hydroxy-8-chloro-1,7-naphthyridine-6-formamido) acetic acid (2.00 g, 5.35 mmol), chloromethyl pivalate (0.96 g, 6.42 mmol), diisopropylethylamine (1.38 g, 10.7 mmol), and N,N-dimethyl formamide (20 mL) were added, heated to 50° C., and reacted for 5 h. The reaction solution was poured into 60 mL of a mixed solution of purified water and ethyl acetate. The system was stirred for 5 min, and set aside for phase separation. The aqueous phase was extracted with ethyl acetate, and the organic phases were combined, and concentrated under reduced pressure. The residue was purified by column chromatography (petroleum ether–ethyl acetate=9-1), and the least polar component was collected, and concentrated under reduced pressure to obtain a white solid (0.50 g, 19.23%).

Specific Physical Characterization Results:

| Example | Compound | State | $^1$H NMR (600 MHz, DMSO/MeOD) δ | MS[M + H]$^+$ |
|---|---|---|---|---|
| 1 | Link-118 | an off-white solid | $^1$H NMR (600 MHz, DMSO-d$_6$) δ: 4.014-4.024(d, J = 6.0 Hz, 2H), 7.318-7.343(t, 1H), 7.388-7.402(d, J = 8.4 Hz, 2H), 7.503-7.529(t, 2H), 7.604-7.619(d, J = 9.0 Hz, 1H), 8.695-8.710(d, J = 9.0 Hz, 1H), 9.235(s, 1H), 12.897(s, 1H), 13.570(s, 1H). | 374.0 |
| 2 | Link-119 | an off-white solid | $^1$H NMR (600 MHz, DMSO-d$_6$) δ: 3.804(s, 3H), 4.012-4.022(d, J = 6.0 Hz, 2H), 7.037-7.051(d, J = 8.4 Hz, 2H), 7.309-7.323(d, J = 8.4 Hz, 2H), 7.556-7.571(d, J = 9.0 Hz, 1H), 8.668-8.683(d, J = 9.0 Hz, 1H) 9.232(s, 1H), 12.941(s, 1H), 13.498(s, 1H). | 404.1 |
| 3 | Link-120 | a light yellow solid | $^1$H NMR (600 MHz, DMSO-d$_6$) δ: 4.014-4.024(d, J = 6.0 Hz, 2H), 7.595-7.617(m, 1H), 7.734-7.750(d, J = 9.6 Hz, 1H), 7.957-7.970(d, J = 7.8 Hz, 1H), 8.556-8.564(d, J = 4.8 Hz, 1H), 8.722(s, 1H), 8.747-8.762(d, J = 9.0 Hz, 1H), 9.233-9.253(t, 1H), 12.842(s, 1H), 13.634(s, 1H). | 375.1 |
| 4 | Link-121 | an off-white solid | $^1$H NMR (600 MHz, DMSO-d$_6$) δ: 4.021-4.030(d, J = 5.4 Hz, 2H), 7.318-7.343(t, 1H), 7.412-7.425(d, J = 7.8 Hz, 2H), 7.505-7.530(t, 2H), 7.592-7.607(d, J = 9.0 Hz, 1H), 8.688-8.703(d, J = 9.0 Hz, 1H), 9.214(s, 1H), 12.846(s, 1H), 13.591(s, 1H). | 417.9 |
| 5 | Link-122 | an off-white solid | $^1$H NMR (600 MHz, DMSO-d$_6$) δ: 4.035-4.045(d, J = 6.0 Hz, 2H), 8.023-8.038(d, J = 9.0 Hz, 1H), 8.736-8.751(d, J = 9.0 Hz, 1H), 9.370(s, 1H), 12.863(s, 1H), 13.752(s, 1H). | 314.0 [M − H] |
| 6 | Link-124 | an off-white solid | $^1$H NMR (600 MHz, DMSO-d$_6$) δ: 4.009-4.019(d, J = 6.0 Hz, 2H), 7.392-7.407(m, 1H), 7.487-7.515(m, 1H), 7.5.38-7.554(m, 1H), | 407.9 |

-continued

| Example | Compound | State | $^{1}$H NMR (600 MHz, DMSO/MeOD) δ | MS[M + H]$^+$ |
|---|---|---|---|---|
| | | | 7.668-7.684(m, 1H), 7.711-7.726(d, J = 9.0 Hz, 1H), 8.747-8.762(d, J = 9.0 Hz, 1H), 9.249(s, 1H), 12.861(s, 1H), 13.591(s, 1H). | |
| 7 | Link-125 | an off-white solid | $^{1}$H NMR (600 MHz, DMSO-d$_6$) δ: 4.019-4.029(d, J = 6.0 Hz, 2H), 7.380-7.407(m, 1H), 7.490-7.518(m, 1H), 7.549-7.564(m, 1H), 7.669-7.699(m, 1H), 8.728-8.743(d, J = 9.0 Hz, 1H), 9.249(s, 1H), 13.267(s, 2H). | 451.9 |
| 8 | Link-126 | an off-white solid | $^{1}$H NMR (600 MHz, DMSO-d$_6$) δ: 4.013-4.023(d, J = 6.0 Hz, 2H), 7.384-7.412(t, 2H), 7.526-7.553(t, 1H), 7.626-7.651(t, 2H), 8.707-8.730(m, 1H), 9.274(s, 1H), 13.235(s, 2H). | 407.9 |
| 9 | Link-127 | an off-white solid | $^{1}$H NMR (600 MHz, DMSO-d$_6$) δ: 4.021-4.031(d, J = 6.0 Hz, 2H), 7.397-7.410(d, J = 7.8 Hz, 2H), 7.526-7.553(t, 1H), 7.619-7.634(d, J = 9.0 Hz, 1H), 7.665-7.667(d, J = 1.2 Hz, 1H), 8.695-8.715(m, 1H), 9.261(s, 1H), 13.198(s, 2H). | 451.9 |
| 10 | Link-128 | an off-white solid | $^{1}$H NMR (600 MHz, DMSO-d$_6$) δ: 3.995-4.005(d, J = 6.0 Hz, 2H), 7.436-7.450(d, J = 8.4 Hz, 2H), 7.555-7.597(m, 3H), 8.699-8.714(d, J = 9.0 Hz, 1H), 9.413(s, 1H), 13.222(s, 2H). | 407.9 |
| 11 | Link-129 | an off-white solid | $^{1}$H NMR (600 MHz, DMSO-d$_6$) δ: 4.022-4.032(d, J = 6.0 Hz, 2H), 7.467-7.481(d, J = 8.4 Hz, 2H), 7.561-7.575(d, J = 8.4 Hz, 2H), 7.619-7.633(d, J = 8.4 Hz, 1H), 8.684-8.699(d, J = 9.0 Hz, 1H), 9.243(s, 1H), 13.261(s, 2H). | 451.9 |
| 12 | Link-130 | an off-white solid | $^{1}$H NMR (600 MHz, DMSO-d$_6$) δ: 4.012-4.022 (d, J = 6.0 Hz, 2H), 7.330-7.359(m, 2H), 7.435-7.457(m, 2H), 7.634-7.649(d, J = 9 Hz, 1H), 8.703-8.717(d, J = 8.4 Hz, 1H), 9.217-9.236(t, 1H), 12.833(s, 1H), 13.603(s, 1H). | 392.0 |
| 13 | Link-131 | a white solid | $^{1}$H NMR (600 MHz, DMSO-d$_6$) δ: 4.019-4.029(d, J = 6.0 Hz, 2H), 7.323-7.365(m, 2H), 7.446-7.481(m, 2H), 7.606-7.621(d, J = 9.0 Hz, 1H), 8.682-8.607(d, J = 9.0 Hz, 1H), 9.238(s, 1H), 13.494(s, 2H). | 436.0 |
| 14 | Link-132 | an off-white solid | $^{1}$H NMR (600 MHz, DMSO-d$_6$) δ: 4.015-4.024(d, J = 5.4 Hz, 2H), 6.842-6.855(d, J = 7.8 Hz, 2H), 7.163-7.176(d, J = 7.8 Hz, 2H), 7.525-7.540(d, J = 9.0 Hz, 1H), 8.652-8.667(d, J = 9.0 Hz, 1H), 9.191-9.200(d, J = 5.4 Hz, 1H), 9.493(s, 1H), 12.805(s, 1H), 13.572(s, 1H). | 390.0 |
| 15 | Link-134 | a pink solid | $^{1}$H NMR (600 MHz, DMSO-d$_6$) δ: 1.428-1.451(t, 3H), 4.026-4.035(d, J = 5.4 Hz, 2H), 4.563-4.598(m, 2H), 7.364-7.379(d, J = 9.0 Hz, 1H), 8.514-8.529(d, J = 9.0 Hz, 1H), 9.185(s, 1H), 12.985(s, 1H), 13.441(s, 1H). | 326.0 |
| 16 | Link-135 | a white solid | $^{1}$H NMR (600 MHz, DMSO-d$_6$) δ: 1.146(s, 9H). 4.145-4.155(d, J = 6.0 Hz, 2H), 5.767(s, 2H), 7.328-7.400(m, 3H), 7.501-7.526(m, 2H), 7.611-7.625(m, 1H), 8.699-8.714(d, J = 9.0 Hz, 1H), 9.393-9.412(m, 1H), 13.430(s, 1H). | 487.9 |

COMPARATIVE EXAMPLE 1

Preparation of [(1-chloro-4-hydroxy-isoquinolinyl-3-carbonyl)-amino]acetic acid

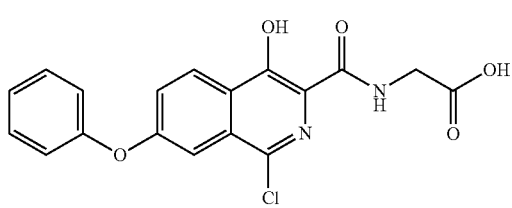 [SMILES: O=C(O)CNC(=O)c1nc(Cl)c2cc(Oc3ccccc3)ccc2c1O]

Step 1: Preparation of methyl 1-chloro-4-hydroxy-7-phenoxy-isoquinoline-3-carboxylate In 50 mL of a reaction flask, methyl 4-hydroxy-7-phenoxy-isoquinoline-3-carboxylate (5.00 g, 16.93 mmol), N-chlorosuccinimide (2.3 g, 17.78 mmol), and acetonitrile (30 mL) were added, heated to 80° C., and reacted for 5 h. The reaction solution was cooled to room temperature, to precipitate out a large amount of solid. The system was stirred at room temperature for 30 min, and subjected to suction filtration. The filter cake was washed with acetonitrile, and dried under vacuum till constant weight 4.43 g.

Step 2: Preparation of [(1-chloro-4-hydroxy-isoquinolinyl-3-carbonyl)-amino]acetic acid In 100 mL of a reaction flask, methyl 1-chloro-4-hydroxy-7-phenoxy-isoquinoline-3-carboxylate (4.43 g, 13.43 mmol), glycine (3.25 g, 40.30 mmol), potassium carbonate (5.57 g, 40.30 mmol), and dimethyl sulfoxide (35 mL) were added, heated to 120° C. and reacted for 4 h. The reaction solution was poured into 150 mL purified water, and extracted with ethyl acetate (100 ml×2). The aqueous phase was adjusted with concentrated hydrochloric acid to a pH of 1~2, and extracted with ethyl acetate (100 ml×2), and the organic phases were combined. The organic phase was washed with water, saturated brine, dried with anhydrous sodium sulfate, and subjected to suction filtration. The filtrate was concentrated under reduced pressure, to obtain an off-white solid, 4.78 g.

$^1$H NMR (600 MHz, DMSO-d$_6$) δ ppm 13.674 (s,1H), 12.850 (s,1H),9.168 (d, J=4.8 Hz, 1H), 8.355-8.383 (m, 1H), 7.694-7.718 (m, 1H), 7.448-7.551 (m, 3H),7.261-7.347 (m, 3H), 4.021(d, J=6.0 Hz, 2H). LCMS: 373.00 [M+H]

COMPARATIVE EXAMPLE 2

Preparation of 2-(5-hydroxy-2-phenoxy-1,7-naphthyridine-6-formamido) acetic acid

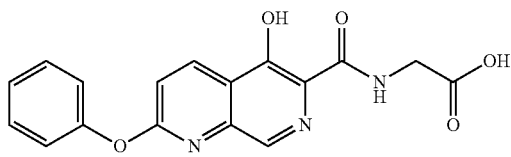 [SMILES: O=C(O)CNC(=O)c1ncc2nc(Oc3ccccc3)ccc2c1O]

In 50 mL of a reaction flask, ethyl 5-hydroxy-2-phenoxy-1,7-naphthyridine-6-carboxylate (1.00 g, 3.225 mmol), glycine (726 m g, 9.674 mmol), potassium carbonate (1.34 g, 9.674 mmol), and dimethyl sulfoxide (20 mL) were added, heated to 120° C. and reacted for 1.5 h. The reaction solution was poured into 100 mL purified water, adjusted with concentrated hydrochloric acid to a pH of 1~2, to precipitate out a large amount of solid. The system was stirred for 30 min, and subjected to suction filtration. The filter cake was washed with purified water, and dried under vacuum till constant weight, to obtain an off-white solid 2-(5-hydroxy-2-phenoxy-1,7-naphthyridine-6-formamido) acetic acid, 950 mg.

$^1$H NMR (600 MHz, DMSO-d$_6$) δ ppm 13.582 (s,1H), 12.976 (s,1H),9.386 (s,1H), 8.669 (d, J=9.0 Hz, 1H), 8.505 (s,1H),7.569(d, J=9.0 Hz, 1H), 7.500-7.525 (m, 2H), 7.320-7.333 (m, 3H), 4.003(d, J=6.0 Hz, 2H). LCMS: 340.02[M+H]

COMPARATIVE EXAMPLE 3

Preparation of [(1-bromo-4-hydroxy-isoquinolinyl-3-carbonyl)-amino]acetic acid

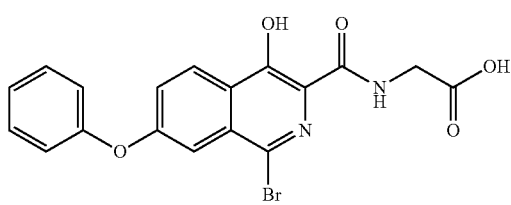 [SMILES: O=C(O)CNC(=O)c1nc(Br)c2cc(Oc3ccccc3)ccc2c1O]

Step 1: Preparation of methyl 1-bromo-4-hydroxy-7-phenoxy-isoquinoline-3-carboxylate In 50 mL of a reaction flask, methyl 4-hydroxy-7-phenoxy-isoquinoline-3-carboxylate (4.98 g, 16.86 mmol), N-bromosuccinimide (3.15 g, 17.71 mmol), and acetonitrile (30 mL) were added, heated to 80° C., and reacted for 6 h. The reaction solution was cooled to room temperature, to precipitate out a large amount of solid. The system was stirred at room temperature for 30 min, and subjected to suction filtration. The filter cake was washed with acetonitrile, and dried under vacuum till constant weight, 4.48 g.

Step 2. Preparation of [(1-bromo-4-hydroxy-isoquinolinyl-3-carbonyl)-amino]acetic acid In 100 mL of a reaction flask, methyl 1-bromo-4-hydroxy-7-phenoxy-isoquinoline-3-carboxylate (4.48 g, 11.97 mmol), glycine (2.70 g, 35.92 mmol), potassium carbonate (4.96 g, 35.92 mmol), and dimethyl sulfoxide (35 mL) were added, heated to 120° C. and reacted for 3.5 h. The reaction solution was poured into 150 mL, purified water, extracted with ethyl acetate (100 ml×2). The aqueous phase was adjusted with concentrated hydrochloric acid to a pH of 1~2, and extracted with ethyl acetate (100 ml×2), and the organic phases were combined. The organic phase was washed with water, saturated brine, dried with anhydrous sodium sulfate, and subjected to suction filtration. The filtrate was concentrated under reduced pressure, to obtain an off-white solid, 4.67 g.

$^1$H NMR (600 MHz, DMSO-d$_6$)δ ppm 13.360 (br,2H), 9.270 (s,1H), 8.335(d, J=9.0 Hz, 1H), 7.680 (d, J=9.0 Hz. 1H), 7.526-7.551 (m, 2H). 7.452 (s,1H),7.334-7.347(d, J=7.8 Hz, 1H),7.264-7.277 (m, 2H),4.006(d, J=5.4 Hz, 2H) LCMS: 416.95 [M+H]

COMPARATIVE EXAMPLE 4

Preparation of 2-(5-hydroxy-8-methyl-2-phenoxy-1,7-naphthyridine-6-formamido) acetic acid

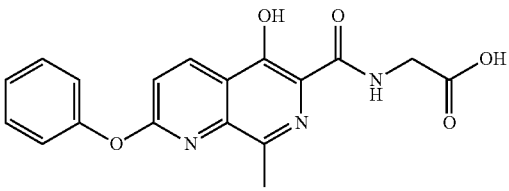 [SMILES: Cc1nc(C(=O)NCC(=O)O)c(O)c2ccc(Oc3ccccc3)nc12]

In 50 mL of a reaction flask, methyl 5-hydroxy-8-methyl-2-phenoxy-1,7-naphthyridine-6-carboxylate (prepared according to the method of Example 1 in CN106146490A) (400 mg, 1.2 mmol), glycine (290 m g, 3.8 mmol), potassium carbonate (534.5 mg, 3.8 mmol), and dimethyl sulfoxide (10 mL) were added, heated to 100° C. and reacted for 2 h. The reaction solution was poured into 50 mL purified water, adjusted with concentrated hydrochloric acid to a pH of 1~2, to precipitate out a large amount of solid. The system was stirred for 30 min, and subjected to suction filtration. The filter cake was washed with purified water, and dried under vacuum till constant weight, to obtain a light yellow solid 2-(5-hydroxy-8-methyl-2-phenoxy-1,7-naphthyridine-6-formamido) acetic acid, 323 mg.

¹H NMR (600 MHz, DMSO-d₆)δ ppm 13.269 (s,1H), 12.844 (s,1H),9.132 (s,1H), 8.613 (d, J=9.0 Hz, 1H), 7.500-7.527 (m, 3H). 7.322-7.374 (m, 3H), 4.042(d, J=6.0 Hz, 2H). 2.521 (s, 3H).
LCMS: 354.04[M+H]

BIOLOGICAL EXAMPLE 1

Effect of Compounds on the Expression of Erythropoietin in Liver Cancer Cells Hep3B In Vitro A test compound was dissolved in dimethyl sulfoxide into a 100 mM stock solution, and then was diluted with 0.5% FBS-containing DMEM medium into 100 μM and 10 μM for later use Human liver cancer cell Hep3B cells were seeded in a 96-well plate with a density of $2.5*10^4$ cells/well. The cells were adherent cultured overnight, and after discarding the used medium. In the 96-well culture plate, the cells were washed once with 0.5% FBS-containing DMEM medium. Each 200 μl of the test compound at concentrations of 100 μM and 10 μM was added to the well, with 2 duplicate wells for each concentration. 0.5% FBS-containing DMEM medium was used instead of the drug solution as the control well. After incubation in a 37° C., 5% $CO_2$ incubator for 24 h, the supernatant was taken as a sample and frozen at −20° C. for later use. An Elisa kit (abeam) was used to detect EPO in the cell supernatant. A microplate reader was used to detect the OD value at 450/620 nm. The results were as follows.

| Compound | EPO level of the compound of the present disclosure/EPO level of FG4592 |
|---|---|
| Link-118 | C |
| Link-119 | A |
| Link-120 | A |
| Link-121 | C |
| Link-122 | A |
| Link-124 | B |
| Link-125 | A |
| Link-126 | A |
| Link-127 | A |
| Link-128 | A |
| Link-129 | A |
| Link-130 | C |
| Link-131 | A |
| Link-134 | A |

Notes:
A represents 0.8 < EPO ratio < 1.1, B represents 1.1 < EPO ratio < 1.3, and C represents EPO ratio ≥ 1.3

The biological activity results showed that the compounds of the present disclosure had an EPO-enhancing effect, at least not less than that of the positive control drug FG4592. Preferably, Link-118, Link-121, Link-124 and Link-130 had more significant EPO-enhancing effect, with the expression of EPO in cells higher than that of the positive control drug FG4592.

BIOLOGICAL EXAMPLE 2

Effect of Compounds on the Expression of Erythropoietin In Vivo (1) 204 c57 mice, male, were divided into 34 groups, 6 mice in each treatment group. The mice in the treatment groups were orally administered once with BAY85-3934, FG-4592, Link-118, Link-119, Link-120, Link-121, Link-122, Link-124, Link-125, Link-126, Link-127, Link-128, Link-129, Link-130, Link-131, Link-134, and Link-135 (10 mg/kg, 50 mg/kg) 6 hours after the administration, blood was taken, and plasma was collected for EPO detection with an ELISA kit (R&D Co.).

The results showed that the compounds of the present disclosure could all promote the expression of erythropoietin in vivo. Among them, Link-138, Link-121, Link-124, Link-129, and Link-130 had higher activity, and they could significantly promote the expression of erythropoietin at 10 mg/kg, with the EPO-enhancing effect all higher titan that of the control samples BAY85-3934 (10 mg/kg) and FG4592 (50 mg/kg).

A represents 1.0<EPO OD value<1.5, B represents 1.5<EPO OD value<2, C represents 2<EPO OD value<3, and D represents EPO OD value>3.

| Drug | Dose (mg/kg) | EPO OD value |
|---|---|---|
| BAY85-3934 | 10 | B |
| FG-4592 | | A |
| Link-118 | | D |
| Link-119 | | A |
| Link-120 | | A |
| Link-121 | | C |
| Link-122 | | A |
| Link-124 | | D |
| Link-125 | | A |
| Link-126 | | A |
| Link-127 | | A |
| Link-128 | | A |
| Link-129 | | D |
| Link-130 | | C |
| Link-131 | | A |
| Link-134 | | A |
| Link-135 | | B |
| BAY85-3934 | 50 | D |
| FG-4592 | | A |
| Link-118 | | D |
| Link-119 | | A |
| Link-120 | | A |
| Link-121 | | D |
| Link-122 | | B |
| Link-124 | | D |
| Link-125 | | D |
| Link-126 | | D |
| Link-127 | | D |
| Link-128 | | D |
| Link-129 | | D |
| Link-130 | | D |
| Link-131 | | A |
| Link-134 | | A |
| Link-135 | | B |

(2) 30 c57 mice, male, were divided into 6 groups, 5 mice in each treatment group. The mice in the treatment groups were orally administered once with Link-138 and Link-121, products prepared according to Comparative Examples 1, 2, 3, and 4 (denoted as compounds of Comparative Examples 1-4) (10 mg/kg). 6 hours after the administration, blood was taken, and plasma was collected for EPO detection with an ELISA kit (R&D Co.).

In order to compare the erythropoietin expression effect of the compounds of the present disclosure with that of the compounds of Comparative Examples 1-4, the EPO ratios of compounds Link118 and Link121 of the present disclosure relative to compounds of Comparative Examples 1-4 were recorded respectively. The results showed that the compounds of the present disclosure could significantly promote the expression of EPO, and their EPO-enhancing effect was significantly higher than that of the compounds of Comparative Examples 1-4.

| Compound of Comparative Example | EPO ratio (Link-118: comparative compound) | EPO ratio (Link-121: comparative compound) |
| --- | --- | --- |
| Comparative Example 1 | 25.37 | 16.50 |
| Comparative Example 2 | 3.17 | 2.06 |
| Comparative Example 3 | 20.3 | 13.20 |
| Comparative Example 4 | 22.55 | 14.67 |

BIOLOGICAL EXAMPLE 3

Effect of Compounds on Reticulocytes of Normal Mice

72 Balb/c mice, male, were divided into 12 groups, 6 mice in each treatment group. In the positive drug control groups: the mice in the FG-4592 treatment groups were orally administered once, at two doses of 10 mg/kg and 50 mg/kg, and the mice in the rhEPO treatment group was intraperitoneaily injected once, at a dose of 100 IU/kg. The compounds of the present disclosure were all orally administered once at a dose of 10 mg/kg. 72 h after the administration, blood was collected from the orbit of all animals, and subjected to EDTA-K2 anticoagulation. Then reticulocytes (RETIC) were counted with an automatic blood cell analyzer. The results showed that, the mice in the FG4592 group of at a dose of 10 mg/kg had no significant difference from normal animals, while the mice treated with other control compounds and the compounds of the present disclosure all had higher reticulocyte counts than that of normal animals ($p<0.05$), with the effect of some compounds better than that of small molecule positive control drug and rhEPO.

| No. | Blank control | FG4592 10 mg/kg p.o., once | FG4592 50 mg/kg p.o., once | rhEPO 100 IU/kg i.p., once | Link-118 10 mg/kg p.o., once | Link-121 10 mg/kg p.o., once |
| --- | --- | --- | --- | --- | --- | --- |
| 1 | 4.1 | 4.7 | 7.1 | 5.9 | 8.0 | 6.4 |
| 2 | 4.5 | 4.9 | 6.2 | 6.6 | 8.7 | 7.2 |
| 3 | 4.7 | 4.7 | 7.4 | 5.9 | 8.1 | 7.7 |
| 4 | 5.0 | 5.0 | 7.9 | 7.1 | 9.7 | 6.7 |
| 5 | 4.6 | 4.6 | 8.0 | 6.6 | 9.8 | 9.1 |
| 6 | 5.4 | 4.5 | 7.9 | 7.4 | 7.4 | 6.6 |
| average | 4.72 | 4.73 | 7.42 | 6.58 | 8.62 | 7.28 |
| SD | 0.44 | 0.19 | 0.69 | 0.61 | 0.97 | 1.01 |
| p1, relative to the control | — | 0.9342 | 0.0000 | 0.0001 | 0.0000 | 0.0002 |
| p2, relative to FG4592, 10 mg/kg | — | — | 0.0000 | 0.0000 | 0.0000 | 0.0001 |
| p3, relative to FG4592, 50 mg/kg | — | 0.0000 | — | 0.0514 | 0.0333 | 0.7946 |
| P4, relative to rhEPO | — | 0.0000 | 0.0514 | — | 0.0015 | 0.1761 |

| No. | Link-124 10 mg/kg p.o., once | Link-125 10 mg/kg p.o., once | Link-126 10 mg/kg p.o., once | Link-127 10 mg/kg p.o., once | Link-128 10 mg/kg p.o., once | Link-129 10 mg/kg p.o., once |
| --- | --- | --- | --- | --- | --- | --- |
| 1 | 6.3 | 5.4 | 6.2 | 5.2 | 5.3 | 8.7 |
| 2 | 7.3 | 6.0 | 6.0 | 5.1 | 5.5 | 7.6 |
| 3 | 7.1 | 5.9 | 5.9 | 5.5 | 6.4 | 7 |
| 4 | 5.5 | 5.4 | 6.1 | 6.8 | 6.6 | 6.6 |
| 5 | 8.0 | 5.8 | 5.1 | 5.9 | 6 | 6.1 |
| 6 | 6.6 | 5.2 | 5.9 | 5.3 | 7.1 | 7.8 |
| average | 6.80 | 5.62 | 5.87 | 5.63 | 6.15 | 7.30 |
| SD | 0.87 | 0.33 | 0.39 | 0.64 | 0.68 | 0.93 |
| p1, relative to the control | 0.0004 | 0.0025 | 0.0008 | 0.0162 | 0.0015 | 0.0001 |
| p2, relative to FG4592, 10 mg/kg | 0.0002 | 0.0002 | 0.0001 | 0.0078 | 0.0006 | 0.0002 |
| p3, relative to FG4592, 50 mg/kg | 0.2030 | 0.0002 | 0.0008 | 0.0009 | 0.0096 | 0.8717 |
| P4, relative to rhEPO | 0.6277 | 0.0065 | 0.0355 | 0.0250 | 0.2739 | 0.0924 |

BIOLOGICAL EXAMPLE 4

Effect of the Compounds on the Expression of HIF-1α and HIF-2α Proteins in Liver Cancer Cells Hep3B In Vitro A test compound was dissolved in dimethyl sulfoxide into a 100 mM stock solution, and then was diluted with 0.5% FBS-containing DMEM medium into 30 μM, 10 μM and 3 μM for later use. Human liver cancer cells Hep3B were seeded in a six-well plate at a density of $2.25*10^5$ cells/well, 2 mL per well. After cultivation overnight, the cells were treated with compounds at different concentrations for 2 h. The proteins were extracted for western blot and further grayscale analysis. The results were as follows:

| Compound | HIF-1α level of the compound of the present disclosure/ HIF-1α level of blank control | HIF-2α level of the compound of the present disclosure/ HIF-2α level of blank control |
| --- | --- | --- |
| Link-118 | D | B |
| Link-121 | B | B |
| Link-124 | B | B |
| Link-125 | B | A |
| Link-129 | A | A |
| Link-130 | B | B |
| Link-131 | B | B |
| Link-134 | A | A |
| FG-4592 | C | C |

Notes:
A represents 1.0 < protein ratio < 4.5, B represents 4.5 < protein ratio < 8.5, C represents 8.5 < protein ratio < 10.0, and D represents protein ratio > 10.0.

The protein level results showed that as compared with the blank control, the HIF-1α and HIF-2α protein expression in the cells treated with Link-138, Link-121, Link-124, Link-325, Link-129, Link-130, Link-131, and Link-134 was all higher than that of the blank control, and all these compounds could promote the expression of HIF-1α and HIF-2α; and the promoting effect on HIF-1α expression of Link-118 was stronger than that of the positive control drug FG4592.

BIOLOGICAL EXAMPLE 5

CYP Enzyme Inhibition Assay

The compounds of the present disclosure were subjected to the CYP450 enzyme inhibition assay. The experimental results showed that the compounds of the present disclosure had low inhibitory activity against CYP1A2, CYP2C9, CYP2C19, CYP2D6 and CYP3A4-M enzymes, and high safety

| Compound | $IC_{50}$ (μM) | | | | |
| --- | --- | --- | --- | --- | --- |
| | CYP1A2 | CYP2C9 | CYP2C19 | CYP2D6 | CYP3A4-M |
| Link-118 | >50 | >50 | >50 | >50 | >50 |
| Link-121 | >50 | >50 | >50 | >50 | >50 |
| Link-124 | >50 | >50 | >50 | >50 | >50 |
| Link-125 | >50 | >50 | >50 | >50 | >50 |
| Link-126 | >50 | >50 | >50 | >50 | >50 |
| Link-127 | 37.9 | >50 | >50 | >50 | >50 |
| Link-128 | >50 | >50 | >50 | >50 | >50 |
| Link-129 | >50 | >50 | >50 | >50 | >50 |

BIOLOGICAL EXAMPLE 6

Cardiotoxic hERG Experiment

Whole-cell patch clamp technique was used to record hERG current. A cell suspension was added to a 35 mm Petri dish, and the dish was then placed on an inverted microscope stage. After the adherence of cells, they were perfused with extracellular fluid at a flow rate of 1-2 mL/min. A glass microelectrode was drawn by a microelectrode puller in two steps, and the pipette tip resistance was between 2-5 MΩ. After establishing the whole cell recording, the clamp potential was held at −80 mV, followed by depolarization to +60 mV when given voltage stimulation and then repolarization to −50 mV to elicit hERG tail current. All recordings were performed after the current was stable. Extracellular perfusion administration started from a low concentration, staying for 5-10 min at each concentration until the current was stable, and then cells were further perfused with the next concentration. In this experiment, Amitriptyline was used as a positive control. The inhibition of each compound on hERG was as follows.

The results of this study showed that the inhibitory effect of Link-118, Link-321, Link-124, Link-125, Link-126, Link-127, Link-128 and Link-129 on hERG current at the highest test concentration (30 μM) was far from the $IC_{50}$ value, indicating that the compounds of the present disclosure had no obvious inhibitory effect on hERG channels. The results of this study could be part of a comprehensive cardiac safety assessment.

$IC_{50}$ Values of the Compounds on Herg Current Recorded on CHO-K1 Stable Cell Line

| Compound | $IC_{50}$ | Number of tested cells | Slope |
| --- | --- | --- | --- |
| Amitriptyline | 3.14 | 3 | 1.26 |
| Link-118 | >30.00 | 3 | — |
| Link-121 | >30.00 | 3 | — |
| Link-124 | >30.00 | 3 | — |
| Link-125 | >30.00 | 3 | — |
| Link-126 | >30.00 | 3 | — |
| Link-127 | >30.00 | 3 | — |
| Link-128 | >30.00 | 3 | — |
| Link-129 | >30.00 | 3 | — |

BIOLOGICAL EXAMPLE 7

SD Rat Residual Kidney Experiment

79 SD rats were subjected to residual kidney surgery after anesthesia (left kidney was resected, one third of the right kidney was left, and the resected kidney part was weighed to confirm the surgical error). After 4 weeks, 45 surviving rats were subjected to blood cell dection and then assigned according to the HCT value 37 rats in good condition were selected and divided into the following groups: Link-118 (5, 10 mg/kg), Link-121 (5, 10 mg/kg), and FG-4592 (10 mg/kg), 6 rats in each treatment group, and 7 in the model group. 4 rats were assigned to the blank control group. The rats were administered three times each week (administered on Monday, Wednesday, and Friday), for 15 times, and blood was taken 24 hours after the last administration (tested by blood routine, blood biochemistry, hepcidin kit).

Conclusion: as compared with the blank control group, the red blood cell (RBC), hemoglobin (HGB), and hematocrit (HCT) of the rats in the model group were significantly decreased, indicating that the model was successfully established. As compared with the model group, Link-118 and FG-4592 both could significantly increase RBC, HGB, and HCT in rats with residual kidney, the efficacy of Link-118 was better than that of FG-4592 at the same dose, and Link-121 could significantly increase HGB and HCT in rats with residual kidney; as compared with the model group, Link-118 and FG-4592 could significantly inhibit hepcidin in rats with residual kidney, and Link-121 reduced hepcidin in rats; as compared with the blank control group, Link-118, Link-121, FG-4592 had no significant effect on liver glutamic-pyruvic aminotransferase and glutamic-oxalacetic transaminase.

BIOLOGICAL EXAMPLE 8

PHD1, PHD2, PHD3 Enzyme Assay

VHL/elongin B/elongin C were constructed, expressed and purified, and VHL was labeled. PHD1, PHD2 and PHD3 were constructed, expressed and purified. VBC protein was labeled with DELFIA Eu-Labeling Kit. A NeutrAvidin 96-well plate was blocked after the addition of 200 μL Blocker Casein to each well, followed by incubation for 30 min. Each well was washed 3 times by adding 200 μL of washing buffer each time. A 200 nM HIF-1a 556-574 solution was prepared with washing buffer, and 100 μL of the solution was added to each well, followed by incubation for 60 min. Each well was washed 3 times by adding 200 μL of washing buffer each time. A 1 mM Biotin solution was prepared with Blocker Casein, and 100 μL of the solution was added to each well, followed by incubation for 30 min. Each well was washed 3 times by adding 200 μL of washing buffer each time. A 20× compound solution was prepared with PHD reaction buffer, with the final concentration of DMSO being 1%. PHD solutions were prepared with PHD reaction buffer, and the concentrations of PHD1, 2, and 3 solutions were 10 ng/μL, 5 ng/μL, and 15 ng/μL, respectively. 95 μL of the PHD solution was added to each compound well, followed by the addition of 5 μL of the compound solution, 95 μL of the PHD solution was added to each full active well, followed by the addition of 5 μL of the PHD reaction buffer; and 100 μL of the PHD reaction buffer was added to each blank well. After mixing homogeneously, the wells were incubated for 60 min. Each well was washed 3 times by adding 200 μL of washing buffer each time A 1 ng/μL Eu-VBC solution was prepared with Eu-VBC binding buffer, and 100 μL of the solution was added to each well, followed by incubation for 60 min. Each well was washed 6 times by adding 200 μL DELFIA Wash Concentrate each time. 100 μL DELFIA Enhancement Solution was added to each well. A microplate reader was used to read TR-Fluorescence at Ex340 and Em615. The flurescence of the sample wells was recorded as FLUsample, the flurescence of the full active wells was recorded as FLU100%, and the flurescence of the blank well was recorded as FLU0%.

The inhibition rate was calculated according to the following formula:

Inhibition rate=$(FLU100\%-FLU\text{sample})/(FLU100\%-FLU0\%)\times100\%$

The experimental results showed that Link-118 and Link-121 had better effect on PHD1, PHD2 and PHD3 than those of compounds of Comparative Examples 1-3.

| Compound | PHD1 ($IC_{50}$ nM) | PHD2 ($IC_{50}$ nM) | PHD3 ($IC_{50}$ nM) |
| --- | --- | --- | --- |
| Link-118 | 46.94 | 207.1 | 72.81 |
| Link-121 | 40.29 | 353.0 | 95.63 |
| Compound of Comparative Example 1 | 272.6 | 770.5 | 560.7 |
| Compound of Comparative Example 2 | 335.2 | 807.2 | 492.2 |
| Compound of Comparative Example 3 | 451.9 | 951.4 | 544.5 |

The embodiments of the present disclosure have been described above. However, the present disclosure is not limited to the above-mentioned embodiments. Any modification, equivalent replacement, improvement and the like made within the spirit and principle of the present disclosure shall be included in the protection scope of the present disclosure Effect of test compounds on various indexes of rats ($\bar{x} \pm sd$)

| Drug | Dose mg/kg | Number of animals (survival/total) | Red blood cells $10^{12}$/L | Hemoglobin (g/L) | Hematocrit | Hepcidin (ng/ml) | Alanine aminotransferase | Glutamic-oxalacetic transaminase |
| --- | --- | --- | --- | --- | --- | --- | --- | --- |
| Link-118 | 5 | 6/6 | 8.05 ± 0.46** | 164 ± 10.99** | 45.88 ± 2.87** | 2.5808 ± 1.0573* | 37.83 ± 1.60 | 116.50 ± 14.43 |
| Link-118 | 10 | 6/6 | 9.61 ± 1.06** | 203.83 ± 22.83**## | 57.2 ± 6.67**## | 2.4472 ± 0.513** | 35.50 ± 6.28 | 113.67 ± 2123 |
| Link-121 | 5 | 5/6 | 7.68 ± 0.46 | 150.60 ± 8.62 | 43 ± 2.26 | 2.8289 ± 0.7597 | 56.40 ± 25.89 | 130.80 ± 3126 |
| Link-121 | 10 | 5/6 | 8.12 ± 1.11 | 163.40 ± 24.44** | 46.86 ± 629** | 2.5494 ± 1.3532 | 47.5 ± 7.23 | 12125 ± 16.11 |
| FG-4592 | 10 | 5/6 | 8.26 ± 0.41** | 16720 ± 8.47** | 47.7 ± 2.19** | 2.59 ± 0.7015* | 40.4 ± 3.58 | 11620 ± 10.96 |
| Model group | — | 7/7 | 6.14 ± 0.91## | 120.33 ± 15.59## | 35.27 ± 4.30## | 4.0069 ± 0.8582 | 49 ± 16.80 | 119.83 ± 25.26 |
| Blank control group | — | 4/4 | 8.36 ± 0.41 | 15825 ± 4.79** | 4525 ± 1.45** | 0.6548 ± 0.2575** | 43.5 ± 8.89 | 171.50 ± 75.77 |

Notes:
as compared with the model group,
*p < 0.05 and
**p < 0.01; as compared with the blank control group,
p < 0.05 and
p < 0.01.

The invention claimed is:

1. A compound of formula (I), tautomer, optical isomer, N-oxide, solvate, or pharmaceutically acceptable salt thereof:

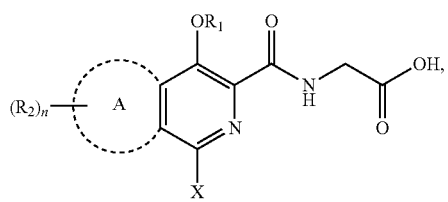

formula (I)

wherein, ring A is a six-membered nitrogen-containing aromatic heterocycle;
$R_1$ is H or $C_1$-$C_6$ alkyl;
$R_2$ is H, halogen, $C_1$-$C_6$ alkyl or Z—$R_3$;
n is 1-3;
Z is O or S;
$R_3$ is selected from $C_6$-$C_{14}$ aromatic ring, 5-14 membered aromatic heterocycle, and unsubstituted or optionally substituted with one or more substituents, the substituents being independently selected from OH, halogen, $C_1$-$C_6$ alkyl, $C_1$-$C_6$ alkoxy, halogen-substituted $C_1$-$C_6$ alkyl, or $R_3$ is selected from H or $C_1$-$C_6$ alkyl;
X is selected from halogen.

2. The compound, tautomer, optical isomer, N-oxide, solvate, or pharmaceutically acceptable salt thereof according to claim 1, wherein the compound is of formula (II)

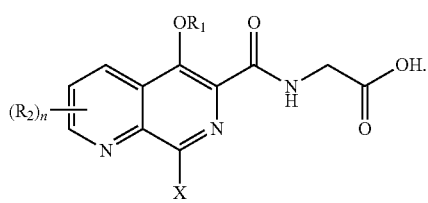

formula (II)

3. The compound, tautomer, optical isomer, N-oxide, solvate, or pharmaceutically acceptable salt thereof according to claim 1, wherein the compound is of formula (III) or formula (IV):

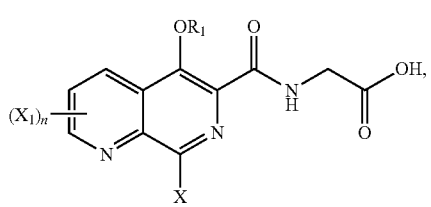

formula (III)

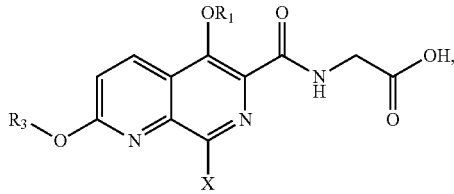

formula (IV)

$X_1$ is independently selected from F, Cl, Br, and I.

4. The compound, tautomer, optical isomer, N-oxide, solvate, or pharmaceutically acceptable salt thereof according to claim 1, wherein ring A is selected from pyridine, pyrazine, pyridazine, pyrrole, and imidazole.

5. The compound, tautomer, optical isomer, N-oxide, solvate, or pharmaceutically acceptable salt thereof according to claim 1, wherein:
$R_1$ is selected from H and $C_1$-$C_4$ alkyl;
$R_2$ is selected from halogen, $C_1$-$C_4$ alkyl, and Z—$R_3$;
n is 1 or 2;
$R_3$ is selected from $C_6$-$C_{14}$ aromatic ring, 5-14 membered aromatic heterocycle, and unsubstituted or substituted with one or more substituents, the substituents being independently selected from OH, halogen, $C_1$-$C_4$ alkyl, $C_1$-$C_4$ alkoxy, and halogen-substituted $C_1$-$C_4$ alkyl, or $R_3$ is a $C_1$-$C_4$ alkyl; and
the halogen is F, Cl, Br, or I.

6. The compound, tautomer, optical isomer, N-oxide, solvate, or pharmaceutically acceptable salt thereof according to claim 3, wherein the compound of formula (III) is of formula (IIIa):

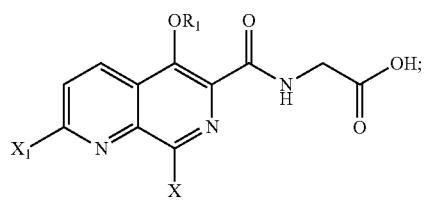

formula (IIIa)

or
the compound of formula (IV) is of formula (V):

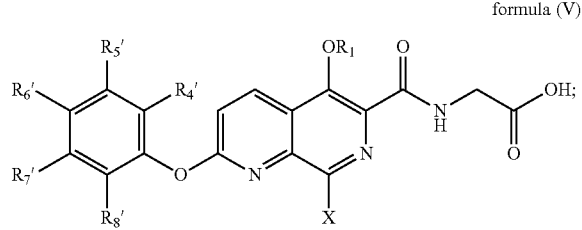

formula (V)

wherein, the $R_1$, X are as defined in the formula IV; and $R_4'$, $R_5'$, $R_6'$, $R_7'$, $R_8'$ are independently selected from H, OH, halogen, $C_1$-$C_6$ alkyl, $C_1$-$C_6$ alkoxy, and halogen-substituted $C_1$-$C_6$ alkyl.

7. The compound, tautomer, optical isomer, N-oxide, solvate, or pharmaceutically acceptable salt thereof according to claim 1, wherein the compound is one of the compounds listed below:

-continued
Link-118
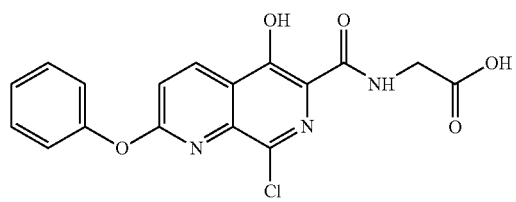
Link-126
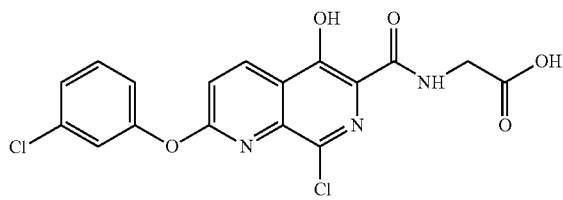
Link-119
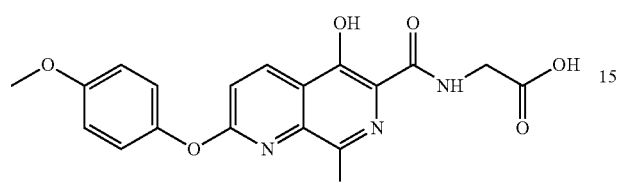
Link-127
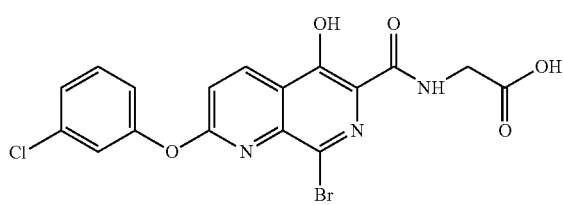
Link-120
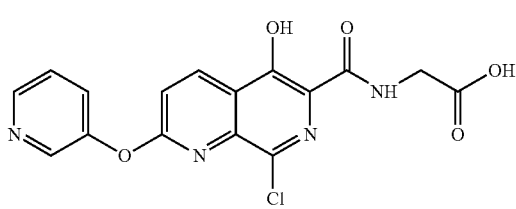
Link-128
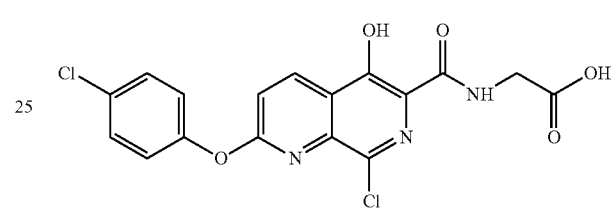
Link-121
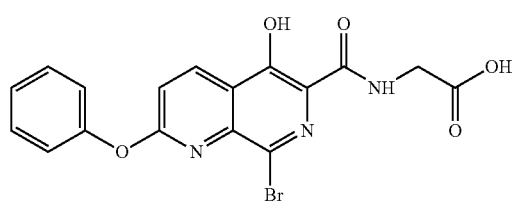
Link-129
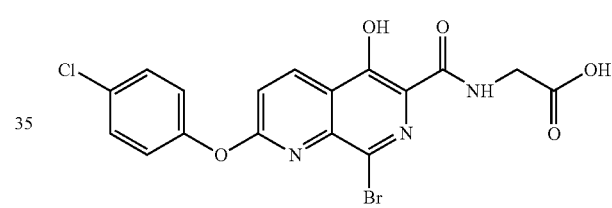
Link-122
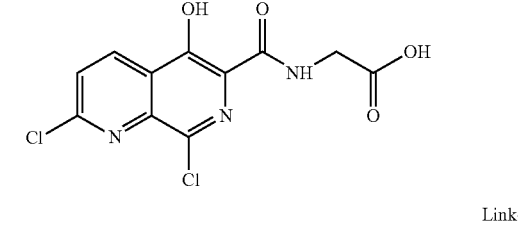
Link-130
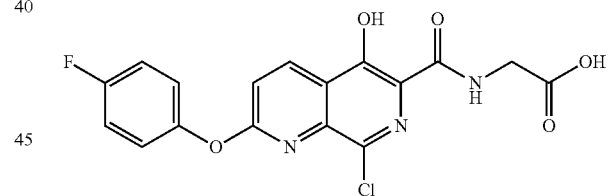
Link-124
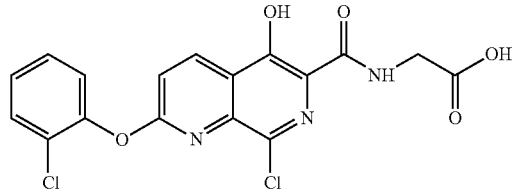
Link-131
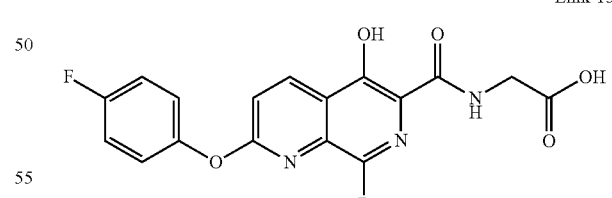
Link-125
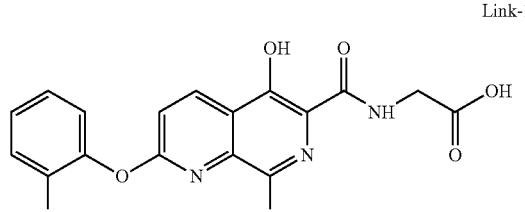
Link-132
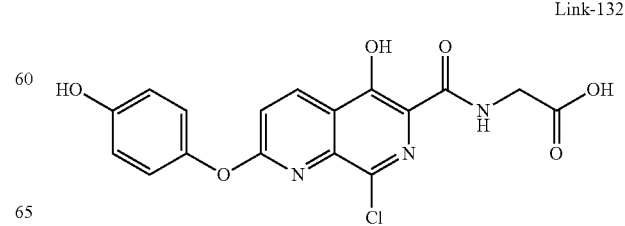

-continued

Link-134

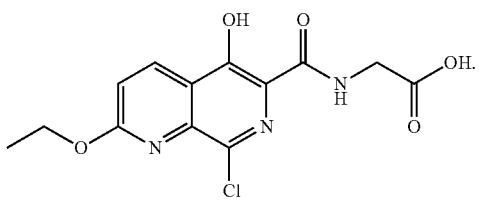

8. A pharmaceutical composition, comprising the compound tautomer, optical isomer, N-oxide, solvate, or pharmaceutically acceptable salt thereof according to claim 1 and a pharmaceutically acceptable carrier.

9. A medicament for treating or alleviating HIF-related and/or EPO-related diseases or conditions in patients, comprising the compound, tautomer, optical isomer, N-oxide, solvate, or pharmaceutically acceptable salt thereof according to claim 1, wherein the HIF-related and/or EPO-related diseases or conditions are one or more selected from anemia, anemia caused by acute or chronic kidney disease, infection, AIDS infection, inflammation, cancer, radiation, toxins, diabetes or surgery, ischemia, myocardial ischemia, angina, myocardial infarction, metabolic disorders, and wound healing diseases in patients.

10. A method for treating or alleviating anemia, anemia caused by acute or chronic kidney disease, infection, AIDS infection, inflammation, cancer, radiation, toxins, diabetes or surgery, ischemia, myocardial ischemia, angina, myocardial infarction, metabolic disorders, or wound healing diseases in patients, or for stabilizing HIFα, promoting endogenous EPO production, increasing iron intake, or increasing iron utilization, comprising administering to a patient in need thereof the compound, tautomer, optical isomer, N-oxide, solvate, or pharmaceutically acceptable salt thereof according to claim 1.

11. The method according to claim 10, wherein the anemic conditions is related to radiation therapy, chemotherapy, dialysis, surgery, abnormal hemoglobin and/or red blood cells, microcytic anemia, hypochromic anemia, aplastic anemia, or renal anemia.

12. A method for preparing the compound according to claim 1, wherein M1 is reacted with halogenation reagent to obtain intermediate M2; and intermediate M2 is reacted with glycine under basic conditions to obtain the compound of formula I,

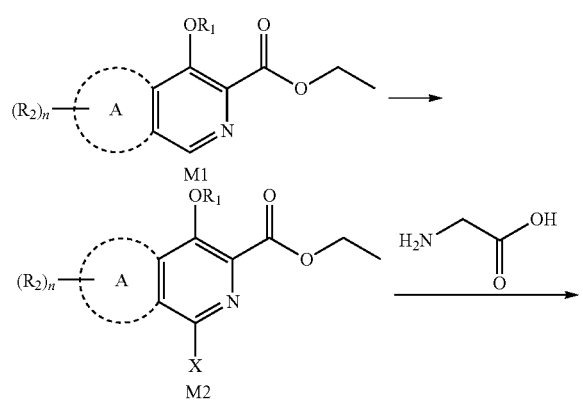

13. A compound, tautomer, optical isomer, N-oxide, solvate, or pharmaceutically acceptable salt thereof, wherein the compound is of formula (Ib):

formula (Ib)

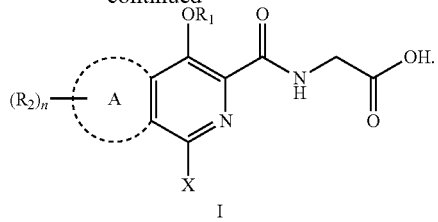

wherein, ring A is a six-membered nitrogen-containing aromatic heterocycle;
$R_1$ is H or $C_1$-$C_6$ alkyl;
$R_2$ is H, halogen, $C_1$-$C_6$ alkyl, or Z—$R_3$;
n is 1-3;
Z is O or S;
$R_3$ is selected from $C_6$-$C_{14}$ aromatic ring, 5-14 membered aromatic heterocycle, and unsubstituted or optionally substituted with one or more substituents, the substituents being independently selected from OH, halogen, $C_1$-$C_6$ alkyl, $C_1$-$C_6$ alkoxy, and halogen-substituted $C_1$-$C_6$ alkyl, or $R_3$ is selected from H and $C_1$-$C_6$ alkyl;
X is a halogen;
$R_4$ is selected from $C_1$-$C_6$ alkyl, and unsubstituted or substituted with $R_5$; and
$R_5$ is selected from $C_1$-$C_6$ alkoxy, $C_1$-$C_6$ alkyl (C=O)—.

14. The compound, tautomer, optical isomer, N-oxide, solvate, or pharmaceutically acceptable salt thereof according to claim 13, wherein the compound is of formula (IIb):

formula (IIb)

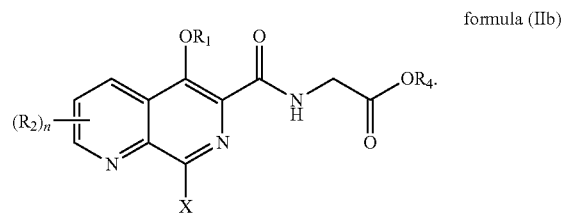

15. The compound, tautomer, optical isomer, N-oxide, solvate, or pharmaceutically acceptable salt thereof according to claim 13, wherein,
the ring A is selected from pyridine, pyrazine, pyridazine, pyrrole and imidazole;
$R_1$ is H or $C_1$-$C_4$ alkyl;
$R_2$ is a halogen, $C_1$-$C_4$ alkyl, or Z—$R_3$; n is selected from 1 or 2;
$R_3$ is selected from $C_6$-$C_{14}$ aromatic ring, 5-14 membered aromatic heterocycle, unsubstituted or optionally substituted with one or more substituents, the substituents being independently selected from OH, halogen, $C_1$-$C_4$ alkyl, $C_1$-$C_4$ alkoxy, halogen-substituted $C_1$-$C_4$ alkyl, or $R_3$ is a $C_1$-$C_4$ alkyl;

$R_4$ is $C_1$-$C_4$ alkyl (C=O)O—$C_1$-$C_4$ alkyl-; and the halogen is F, Cl, Br, or I.

16. The compound, tautomer, optical isomer, N-oxide, solvate, or pharmaceutically acceptable salt thereof according to claim 13, wherein the compound is of formula (IIIb) or formula (IVb):

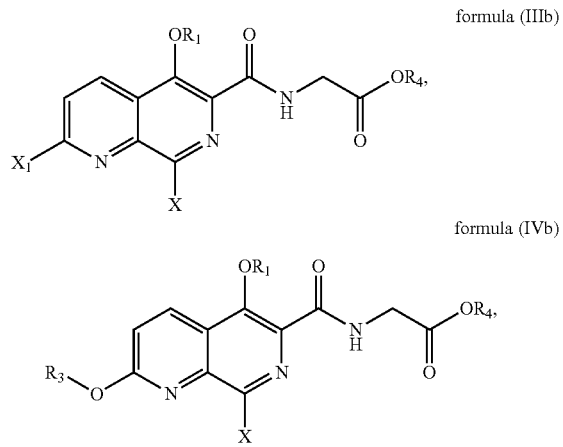

formula (IIIb)

formula (IVb)

wherein $X_1$ is independently selected from F, Cl, Br, and I.

17. The compound, tautomer, optical isomer, N-oxide, solvate, or pharmaceutically acceptable salt thereof according to claim 13, wherein the compound is of formula (Vb) or formula (VIb):

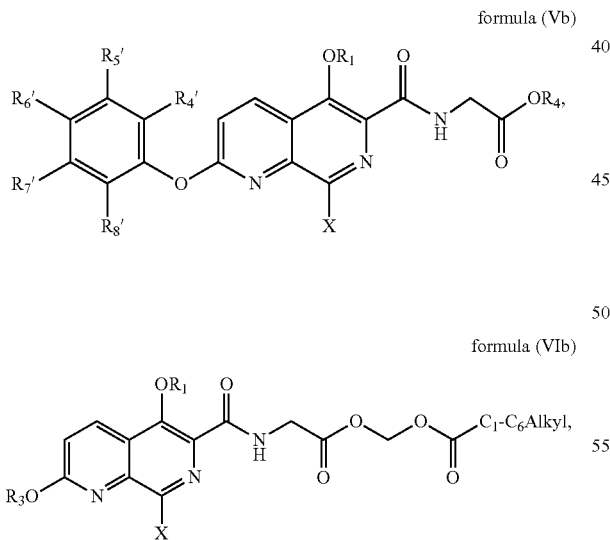

formula (Vb)

formula (VIb)

wherein $R_4'$, $R_5'$, $R_6'$, $R_7'$, $R_8'$ are independently selected from H, OH, halogen, $C_1$-$C_6$ alkyl, $C_1$-$C_6$ alkoxy, and halogen-substituted $C_1$-$C_6$ alkyl.

18. The compound, tautomer, optical isomer, N-oxide, solvate, or pharmaceutically acceptable salt thereof according to claim 13, wherein the compound is

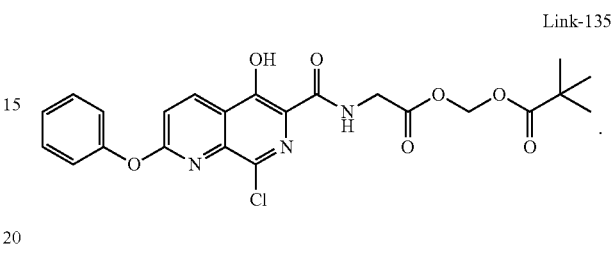

Link-135

19. A method for treating or alleviating anemia, anemia caused by acute or chronic kidney disease, infection, AIDS infection, inflammation, cancer, radiation, toxins, diabetes or surgery, ischemia, myocardial ischemia, angina, myocardial infarction, metabolic disorders, or wound healing diseases in patients, comprising administering to a patient in need thereof the compound, tautomer, optical isomer, N-oxide, solvate, or pharmaceutically acceptable salt thereof according to claim 7.

20. A compound of formula M15:

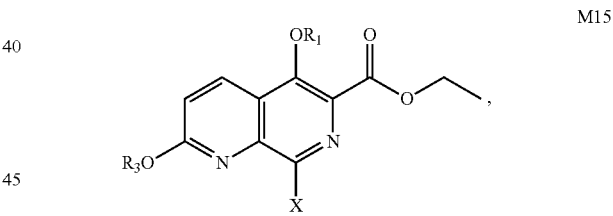

M15 wherein, $R_1$ is selected from H or $C_1$-$C_6$ alkyl;

$R_3$ is selected from $C_6$-$C_{14}$ aromatic ring, 5-14 membered aromatic heterocycle, unsubstituted or optionally substituted with one or more substituents, the substituents being independently selected from OH, halogen, $C_1$-$C_6$ alkyl, $C_1$-$C_6$ alkoxy, and halogen-substituted $C_1$-$C_6$; or $R_3$ is selected from hydrogen and $C_1$-$C_6$ alkyl; and X is selected from F, Cl, Br, and I.

* * * * *